United States Patent

Moser et al.

Patent Number: 4,919,704
Date of Patent: Apr. 24, 1990

[54] 4,5,6,7-TETRAHYDROISOINDOLE-1,3-DIONES

[75] Inventors: Hans Moser, Rheinfelden; George Pissiotas, Lovrach; Hans-Georg Brunner, Lausen, all of Switzerland

[73] Assignee: Ciba-Geigy Corporation, Ardsley, N.Y.

[21] Appl. No.: 226,701

[22] Filed: Aug. 1, 1988

[30] Foreign Application Priority Data

Aug. 14, 1987 [CH] Switzerland ............... 3132/87-9

[51] Int. Cl.$^5$ ............... A01N 37/32; C07D 209/48
[52] U.S. Cl. ............................ 71/96; 71/95; 548/513
[58] Field of Search .................. 548/513; 71/95, 96

[56] References Cited

U.S. PATENT DOCUMENTS

| | | | |
|---|---|---|---|
| 3,984,435 | 10/1976 | Matsui | 548/513 |
| 4,431,822 | 2/1984 | Nagana et al. | 548/513 |
| 4,484,940 | 11/1984 | Nagano et al. | 71/96 |
| 4,536,209 | 8/1985 | Jikihara | 548/513 |
| 4,594,099 | 6/1986 | Yamada | 548/513 |

FOREIGN PATENT DOCUMENTS

| | | |
|---|---|---|
| 1163635 | 3/1984 | Canada . |
| 061741 | 10/1982 | European Pat. Off. . |
| 0068822 | 1/1983 | European Pat. Off. . |
| 190755 | 2/1986 | European Pat. Off. . |
| 207894 | 6/1986 | European Pat. Off. . |
| 216243 | 9/1986 | European Pat. Off. . |
| 3013162 | 10/1980 | Fed. Rep. of Germany . |
| 3109035 | 7/1982 | Fed. Rep. of Germany . |
| 3737152 | 5/1988 | Fed. Rep. of Germany . |
| 3743127 | 6/1988 | Fed. Rep. of Germany . |
| 0280471 | 12/1986 | Japan . |

OTHER PUBLICATIONS

Chem. Abstract, vol. 74, 111779h.

Primary Examiner—John W. Rollins
Assistant Examiner—Frederick F. Tsung
Attorney, Agent, or Firm—Kevin T. Mansfield

[57] ABSTRACT

There are disclosed novel herbicidally active pyrrolidine-2,5-diones and 4,5,6,7-tetrahydroisoindole1,3-diones of formula

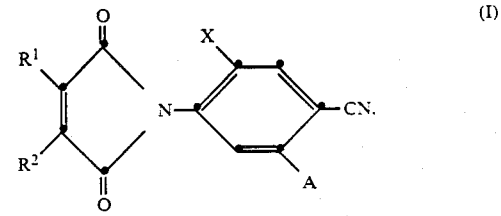

wherein
$R^1$ is hydrogen; or $C_1$-$C_4$alkyl;
$R^2$ is $C_1$-$C_4$alkyl; or
$R^1$ and $R^2$, when taken together, are a $(CH_2)_4$ group which may be substituted by one or two $C_1$-$C_4$alkyl groups;
X is hydrogen; or halogen;
A is

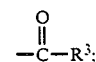

or O—$R^4$;
$R^3$ is hydroxy; ($C_1$-$C_8$)-alkoxy; ($C_1$-$C_4$)-alkoxy-($C_1$-$C_4$)-alkoxy-($C_1$-$C_4$)-akoxy; ($C_1$-$C_4$)-alkylthio-($C_1$-$C_4$)-alkoxy; mono- or di($C_1$-$C_4$)-alkylamino-($C_1$-$C_4$)-alkoxy; ($C_1$-$C_8$)-cyanoalkoxy; ($C_3$-$C_8$)-alkenyloxy; ($C_3$-$C_8$)-haloalkenyloxy; ($C_3$-$C_8$)-alkynyloxy; ($C_3$-$C_7$)-cycloalkoxy; ($C_3$-$C_7$)-cycloalkyl-($C_1$-$C_4$)-alkoxy; halo($C_3$-$C_7$)-cycloalkoxy; unsubstituted or substituted benzyloxy, phenoxy or phenylthio; the salt groups —O—Na, —O—K, —O—(Ca)$_{0.5}$, —O—(Mg)$_{0.5}$ or —O—NH$_4$; amino; unsubstituted or substituted ($C_1$-$C_4$)-alkylamino or di($C_1$-$C_4$)-alkylamino; ($C_3$-$C_4$)-alkenylamino; diallylamino; N-pyrrolidino; N-piperidino; N-morpholino; N-thiomorpholino; N-piperidazino; ($C_1$-$C_8$)-alkylthio; ($C_3$-$C_8$)-alkenylthio; benzylthio; unsubstituted or substituted ($C_1$-$C_4$)-alkylthio or ($C_1$-$C_4$)-alkoxy;
$R^4$ is ($C_1$-$C_8$)-alkyl; ($C_3$-$C_7$)-cycloalkyl; ($C_3$-$C_7$)-cycloalkyl-($C_1$-$C_4$)-alkyl; ($C_3$-$C_7$)-halocycloalkyl; ($C_1$-$C_8$)-alkylcarbonyl; allylcarbonyl; unsubstituted or substituted benzylcarbonyl, benzoyl or dioxolanyl; furoyl; thienoyl; unsubstituted or substituted $C_1$-$C_4$alkyl.

The invention further relates to the preparation of the compounds of formula I, to herbicidal compositions containing them and to the use thereof as herbicides and plant growth regulators, and to novel intermediates for the preparation of these compounds.

7 Claims, No Drawings

4,5,6,7-TETRAHYDROISOINDOLE-1,3-DIONES

The present invention relates to novel 1-phenylpyrrolidine-2,5-diones and 2-phenyl-4,5,6,7-tetrahydroisoindole-1,3-diones of the general formula I below which are mandatorily substituted in the 4-position of the phenyl ring by a cyano group. The invention further relates to the preparation of these novel compounds and to novel intermediates.

The compounds of formula I are herbicidally active and have, in particular, selective herbicidal properties. The invention accordingly also relates to herbicidal compositions which contain compounds of formula I and to the use thereof as herbicides, as well as to methods of controlling undesirable plant growth.

Specifically, the present invention relates to novel compounds of formula I.

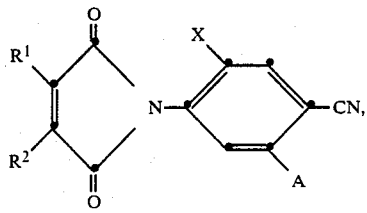

wherein
$R^1$ is hydrogen; or $(C_1-C_4)$-alkyl;
$R^2$ is $(C_1-C_4)$-alkyl; or $R^1$ and $R^2$, when taken together, are a $(CH_2)_4$ group which may be substituted by one or two $(C_1-C_4)$-alkyl groups;
X is hydrogen; or halogen;
A is

or $O-R^4$;
$R^3$ is hydroxy; $(C_1-C_8)$-alkoxy; $(C_1-C_4)$-alkoxy-$(C_1-C_4)$-alkoxy; $(C_1-C_4)$-alkylthio-$(C_1-C_4)$-alkoxy; mono- or di$(C_1-C_4)$-alkylamino-$(C_1-C_4)$-alkoxy; $(C_1-C_8)$-cyanoalkoxy; $(C_3-C_8)$-alkenyloxy; $(C_3-C_8)$-haloalkenyloxy; $(C_3-C_8)$-alkynyloxy; $(C_3-C_7)$-cycloalkoxy; $(C_3-C_7)$-cycloalkyl-$(C_1-C_4)$-alkoxy; halo-$(C_3-C_7)$-cycloalkoxy; benzyloxy or benzyloxy which is substituted in the pheny nucleus by a member selected from the group consisting of halogen, $(C_1-C_4)$-alkyl, $(C_1-C_4)$-alkoxy, $(C_1-C_4)$-haloalkyl, cyano and nitro; phenoxy; halophenoxy; $(C_1-C_4)$-alkylphenoxy; $(C_1-C_4)$-alkoxyphenoxy; $(C_1-C_4)$-haloalkylphenoxy; cyanophenoxy; nitrophenoxy; phenylthio; halophenylthio; $(C_1-C_4)$-alkylphenylthio; $(C_1-C_4)$-alkoxyphenylthio; $(C_1-C_4)$-haloalkylthio; cyanophenylthio; nitrophenylthio; the salt groups $-O-Na$, $-O-K$, $-O-(Ca)_{0.5}$, $-O-(Mg)_{0.5}$ or $-O-NH_4$; amino; $(C_1-C_4)$-alkylamino; di-$(C_1-C_4)$-alkylamino; $(C_2-C_4)$-haloalkylamino; di-$(C_2-C_4)$-haloalkylamino; $(C_1-C_4)$-hydroxyalkylamino; di-$(C_1-C_4)$-hydroxyalkylamino; $(C_3-C_4)$-alkenylamino; diallylamino; N-pyrrolidino; N-piperidino; N-morpholino; N-thiomorpholino; N-piperidazino; $(C_1-C_8)$-alkylthio; $(C_3-C_8)$-alkenylthio; benzylthio; $(C_1-C_4)$-alkylthio substituted by $(C_1-C_8)$-alkoxycarbonyl, $(C_1-C_4)$-alkoxy-$(C_1-C_4)$-alkoxycarbonyl, $(C_3-C_8)$-alkenyloxycarbonyl, $(C_3-C_8)$-alkynyloxycarbonyl, $(C_1-C_8)$-alkylthiocarbonyl, $(C_3-C_8)$-alkenylthiocarbonyl or $(C_3-C_8)$-alkylnylthiocarbonyl; or $(C_1-C_4)$-alkoxy substituted by $(C_1-C_8)$-alkoxycarbonyl, $(C_1-C_4)$-alkoxy-$(C_1-C_4)$-alkoxycarbonyl, $(C_3-C_8)$-alkenyloxycarbonyl, $(C_3-C_8)$-alkynyloxycarbonyl, $(C_1-C_8)$-alkylthiocarbonyl, $(C_3-C_8)$-alkenylthiocarbonyl, $(C_3-C_8)$-alkynylthiocarbonyl, $(C_1-C_4)$-alkylcarbamoyl, di-$(C_1-C_4)$-alkylcarbamoyl or phenylcarbamoyl which is unsubstituted or substituted in the phenyl nucleus by a member selected from the group consisting of halogen $(C_1-C_4)$-alkyl, $(C_1-C_4)$-alkoxy, $(C_1-C_4)$-haloalkyl, cyano and nitro;
$R^4$ is $(C_1-C_8)$-alkyl; $(C_1-C_4)$-alkoxy-$(C_1-C_4)$-alkyl; $(C_1-C_4)$-alkylthio-$(C_1-C_4)$-alkyl; mono- or di-$(C_1-C_4)$-alkylamino-$(C_1-C_4)$-alkyl; $(C_1-C_4)$-haloalkyl; $(C_1-C_8)$-cyanoalkyl; $(C_3-C_8)$-alkenyl; $(C_3-C_8)$-haloalkenyl; $(C_3-C_8)$-alkynyl; $(C_3-C_7)$-cycloalkyl; $(C_3-C_7)$-cycloalkyl-$(C_1-C_4)$-alkyl; $(C_3-C_7)$-halocycloalkyl; $(C_1-C_8)$-alkylcarbonyl; allylcarbonyl; benzylcarbonyl or benzylcarbonyl which is substituted in the phenyl ring by a member selected from the group consisting of halogen, $(C_1-C_4)$-alkyl, $(C_1-C_4)$-alkoxy, $(C_1-C_4)$-haloalkyl, cyano and nitro; $(C_3-C_7)$-cycloalkylcarbonyl; benzoyl or benzoyl which is substituted in the phenyl ring by a member selected from the group consisting of halogen, $(C_1-C_4)$-alkyl, $(C_1-C_4)$-alkoxy, $(C_1-C_4)$-haloalkyl, cyano and nitro; furoyl; thienoyl; $(C_1-C_4)$-alkyl substituted by phenyl, halophenyl, $(C_1-C_4)$-alkylphenyl, $(C_1-C_4)$-alkoxyphenyl, $(C_1-C_4)$-haloalkylphenyl, $(C_1-C_4)$-haloalkoxyphenyl, nitrophenyl, cyanophenyl, $(C_1-C_8)$-alkoxycarbonyl, $(C_1-C_4)$-alkoxy-$(C_1-C_4)$-alkoxycarbonyl, $(C_3-C_8)$-alkenyloxycarbonyl, $(C_3-C_8)$-alkynyloxycarbonyl, $(C_1-C_8)$-alkylthiocarbonyl, $(C_3-C_8)$-alkenylthiocarbonyl, $(C_3-C_8)$-alkynylthiocarbonyl, carbamoyl, $(C_1-C_4)$-alkylcarbamoyl, di-$(C_1-C_4)$-alkylcarbamoyl, hydroxy, phenylcarbamoyl or phenylcarbamoyl which is substituted in the phenyl ring by a member selected from the group consisting of halogen, $(C_1-C_4)$-alkyl, $(C_1-C_4)$-alkoxy, cyano, nitro and $(C_1-C_4)$-haloalkyl; dioxolan-2-yl, unsubstituted or substituted by one or two $(C_1-C_4)$-alkyl groups; or 1,3-dioxolan-2-yl, unsubstituted or substituted by one or two $(C_1-C_4)$-alkyl groups.

The generic terms used in the foregoing definitions encompass, for example, the following specific individual substituents without implying any restriction of the invention to this recitation:

Alkyl denotes methyl, ethyl, n-propyl, isopropyl, n-butyl, isobutyl, sec-butyl and tert-butyl. Methyl and ethyl are preferred.

Halogen is fluorine, chlorine, bromine and iodine. Fluorine and chlorine are preferred.

Alkoxy denotes methoxy, ethoxy, propoxy, isopropoxy, n-butoxy, isobutoxy, sec-butoxy and tert-butoxy. Methoxy and ethoxy are preferred.

Haloalkyl denotes fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl. Chloromethyl, 2-chloroethyl and trifluoromethyl are preferred.

Haloalkoxy is fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy. Difluoromethoxy, 2-chloroethoxy and trifluoromethoxy are preferred.

Alkoxycarbonyl is methoxycarbonyl, ethoxycarbonyl, 4-propoxycarbonyl, isopropoxycarbonyl and n-butoxycarbonyl. Methoxycarbonyl and ethoxycarbonyl are preferred.

Alkoxyalkyl is methoxymethyl, ethoxymethyl, propoxymethyl, methoxyethyl, ethoxyethyl, propoxyethyl, methoxypropyl, ethoxypropyl or propoxypropyl.

Alkylthioalkyl is mehtylthiomethyl, ethylthiomethyl, methylthioethyl, ethylthioethyl or iospropylthioethyl.

Alkylaminoalkyl is methylaminoethyl, dimethylaminoethyl, ethylaminoethyl or diethylaminoethyl.

Cyanoalkyl is cyanomethyl, cyanoethyl or cyanopropyl.

Alkenyl is allyl, 2-butenyl, 3-butenyl or methallyl. Allyl is prferred.

Alkynyl is propargyl, 2-butynyl or 3-butynyl. Propargyl is preferred.

Cycloalkyl is cyclopropyl, cyclobutyl, cyclopentyl, cyclohexyl or cycloheptyl. Cyclopentyl or cyclohexyl are preferred.

Halocycloalkyl is 2,2-dichlorocyclopropyl or pentachlorocyclohexyl.

Alkylsulfonyl is methylsulfonyl, ethylsulfonyl, propylsulfonyl or butylsulfonyl. Methylsulfonyl and ethysulfonyl are preferred.

Cycloalkoxycarbonyl is cyclopentoxycarbonyl or cyclohexoxycarbonyl.

Phenyl by itself or as moiety of another substituent such as phenoxy, phenylthio, phenoxycarbonyl, phenylcarbamoyl, benzyl or benzoyl, may generally be unsubstituted or may contain a further substituent. The substitutents can then be in ortho-, meta- or para-position. Preferred positions are ortho and para to the point of attachment at the ring. Preferred substituents are halogen atoms.

The individual moieties of further substituents which are composed of several moieties are as defined in accordance with the examples given above. These definitions too have purely illustrative character and in no way imply any restriction of the invention.

Preferred compounds of formula I are those wherein
$R^1$ is hydrogen; or $(C_1-C_4)$-alkyl;
$R^2$ is $(C_1-C_4)$-alkyl; or
$R^1$ and $R^2$, when taken together, are a $(CH_2)_4$ group which may be substituted by a $(C_1-C_4)$-alkyl group;
X is hydrogen; fluorine; chlorine; or bromine;
A is

or O—$R^4$;
$R^3$ is hydroxy; $(C_1-C_5)$-alkoxy; $(C_1-C_4)$-alkoxy-$(C_1-C_4)$-alkoxy; $(C_1-C_4)$-alkylthio-$(C_1-C_4)$-alkoxy; mono- or di$(C_1-C_4)$-alkylamino-$(C_1-C_4)$-alkoxy; $(C_1-C_4)$-cyanoalkoxy; $(C_3-C_5)$-haloalkenyloxy; $(C_3-C_5)$-alkynyloxy; $(C_3-C_5)$-alkenyloxy; $(C_3-C_6)$-cycloalkylmethoxy; the salt groups —O—Na, —O—K, —O—$(Ca)_{0.5}$, —O—$(Mg)_{0.5}$ or —O—$NH_4$; amino; di$(C_1-C_4)$-alkylamino; diallylamino; benzyloxy; N-piperidino; N-morpholino; N-thiomorpholino; $(C_1-C_4)$-alkylthio; $(C_1-C_4)$-alkylthio substituted by $(C_1-C_4)$-alkoxycarbonyl; $(C_1-C_4)$-alkoxy substituted by $(C_1-C_4)$-alkoxycarbonyl, $(C_1-C_4)$-alkylthiocarbonyl, $(C_1-C_4)$-alkylcarbamoyl or di$(C_1-C_4)$alkylcarbamoyl;

$R^4$ is $(C_1-C_5)$-alkyl; $(C_1-C_4)$-alkoxy-$(C_1-C_4)$-alkyl; $(C_1-C_4)$-alkylthio-$(C_1-C_4)$-alkyl; $(C_1-C_4)$-haloalkyl; $(C_3-C_5)$-alkenyl; $(C_3-C_5)$-haloalkenyl; $(C_3-C_5)$-alkynyl; cyclohexylmethyl; $(C_1-C_4)$-alkylcarbonyl; benzoyl; unsubstituted or monosubstituted in the phenyl ring by a member selected from the group consisting of fluorine, chlorine, $(C_1-C_4)$-alkyl, $(C_1-C_4)$-alkoxy, cyano and nitro; $(C_1-C_4)$-alkyl which is monosubstituted by a member selected from the group consisting of phenyl, $(C_1-C_4)$-alkoxycarbonyl, $(C_1-C_4)$-alkylthiocarbonyl, carbamoyl, di-$(C_1-C_4)$-alkylcarbamoyl and hydroxy.

Particularly preferred compounds of formula I are those wherein
$R^1$ is hydrogen; methyl; or ethyl;
$R^2$ is methyl or ethyl; or
$R^1$ and $R^2$, when taken together, are a $(CH_2)_4$ group which may be substituted by a methyl group;
X is hydrogen; fluorine; or chlorine;
A is

or —O—$R_4$;
$R^3$ is hydroxy; $(C_1-C_5)$-alkoxy; $(C_1-C_2)$-alkoxy-$(C_1-C_2)$-alkoxy; $(C_1-C_4)$-alkylthio-$(C_1-C_3)$-alkoxy; dimethylamino-$(C_1-C_3)$-alkoxy; allyloxy; chloroallyloxy; propargyloxy; cyclopropylmethoxy; cyclohexylmethoxy; the salt groups —O—Na, —O—K, —O—$(Ca)_{0.5}$, —O—$(Mg)_{0.5}$ or —O—$NH$; dimethylamino; diallylamino; N-morpholino; methylthio; $(C_1-C_2)$-alkylthio which is monosubstituted by a $(C_1-C_3)$-alkoxycarbonyl group; $(C_1-C_2)$-alkoxy which is monosubstituted by $(C_1-C_4)$-alkoxycarbonyl, $(C_1-C_3)$-alkylthiocarbonyl or N,N-dimethylcarbamoyl;

$R^4$ is $(C_1-C_5)$-alkyl; methoxyethyl; $(C_1-C_3)$-alkylthio-$(C_1-C_3)$-alkyl; allyl; chloroallyl; propargyl; cyclohexylmethyl; acetyl; behzoyl; $(C_1-C_3)$-alkyl which is monosubstituted by a member selected from the group consisting of phenyl, $(C_1-C_4)$-alkoxycarbonyl, methylthiocarbonyl, carbamoyl, N,N-dimethylcarbamoyl and hydroxy.

Compounds of formula I meriting special mention are those in which X is fluorine or hydrogen.

Further preferred compounds of formula I are those wherein $R^4$ is isopropyl, and those wherein $R^3$ is sec-butyl.

Preferred individual compounds are 1-(4-cyano-2-fluoro-5-isopropoxyphenyl)-3,4-dimethylpyrrole-(1H)2,5-dione, 2-(5-carboxy-4-cyano-2-fluoropheny)-4,5,6,7-tetrahydroisoindole-(2H)1,3-dione, 2-(4-cyano-2-fluoro-5-n-propoxycarbonylphenyl)-4,5,6,7-tetrahydroisoindole-(2H)1,3-dione, 2-(5-n-butoxycarbonyl-4-cyano-2-fluorophenyl)-4,5,6,7-tetrahydroisoindole-(2H)1,3-dione, 2-(4-cyano-2-fluoro-5-isopropoxyphenyl)-5-methyl-4,5,6,7-tetrahydroisoindole-(2H)1,3-dione, 1-(4-cyano-2-fluoro-5-isopropoxyphenyl)-3-ethyl-4-methyl-pyrrole-(1H)2,5-dione, 2-(4-cyano-2-fluoro-5-ispropoxyphenyl)-4,5,6,7-tetrahydroisoindole-(2H)1,3-dione, 2-(4-cyano-2-fluoro-5-isopropoxycarbonylphenyl)-4,5,6,7-tetrahydroisoindole-(2H)1,3-dione, and 2-(5-sec-butoxycarbonyl-4-cyano-2-fluorophenyl)-4,5,6,7-tetrahydroisoindole-(2H)1,3-dione.

The compounds of formula I can be prepared by methods in accordance with those described in the literature by (a) reacting a furan-2,5-dione of formula II with an aniline III

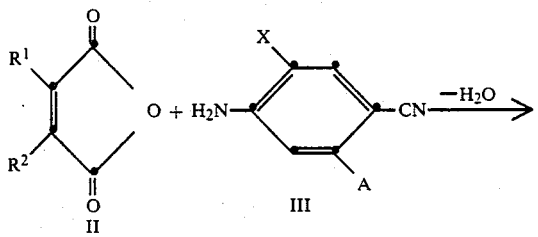

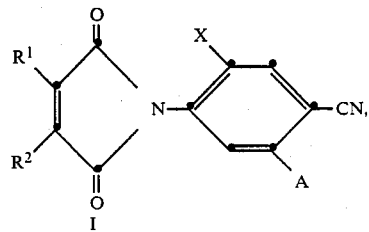

wherein $R^1$, $R^2$, X and A are as previously defined; or (b) in a compound of formula IV

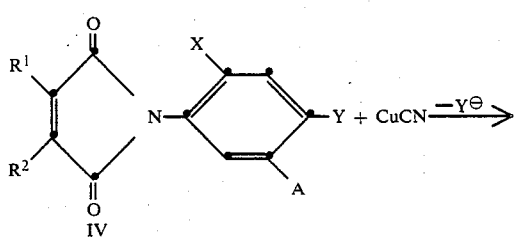

wherein $R^1$, $R^2$, X and A have the given meanings and Y is chlorine, bromine or iodine, replacing halogen with cyano by reaction with CuCN.

Further, compounds of formula Ia, wherein A is $COR^3$, can be prepared by:

(c) condensing a compound of formula V, wherein $R^1$, $R^2$ and X have the given meanings

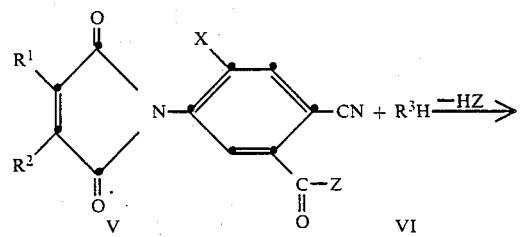

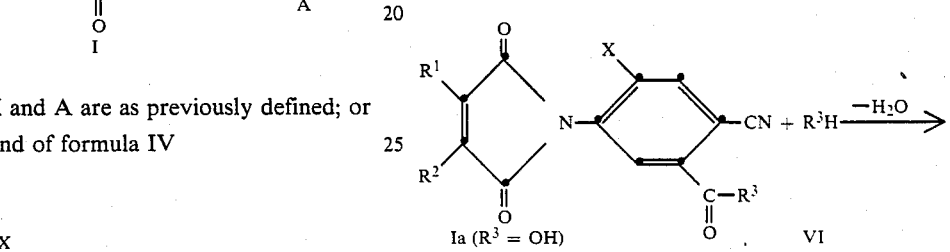

and Z is a group which can be replaced under the reaction conditions, for example halogen or $C_1$-$C_4$alkylcarbonyloxy, with a compound of formula VI, wherein $R^3$ is as previously defined above; or (d) esterifying a carboxylic acid of formula Ia, wherein $R^1$, $R^2$ and X have the given meanings and $R^3$ is OH, with an alcohol or thioalcohol of formula VI

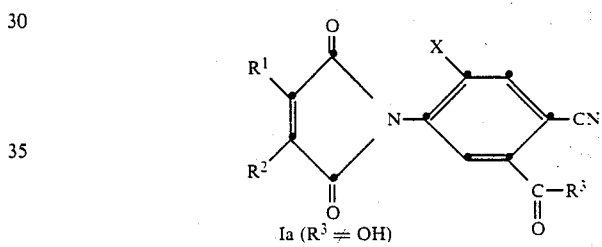

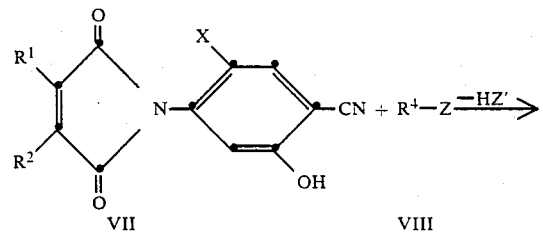

preferably in the presence of a dehydrating or water binding agent.

Compounds of formula Ib, wherein A is $OR^4$, can also be prepared by methods known per se by (e) etherifying a phenol of formula VII, wherein $R^1$, $R^2$ and X have the given meanings

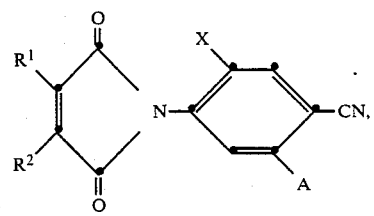

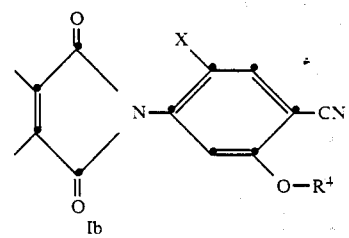

with a compound of formula VIII, wherein $R^4$ has the given meanings and Z is a group which can be removed under the reaction conditions, for example a halogen atom or a phenylsulfonyloxy or alkylated phenylsulfonyloxy group.

The above reactions are conveniently carried out in an inert solvent. Examples of suitable inert solvents are: hydrocarbons such as benzene, toluene or xylene; ethers such as diethyl ether, methyl isopropyl ether, glymes, diglymes; cyclic ethers such as tetrahydrofuran and dioxane; ketones such as acetone, methyl ethyl ketone; amides such as dimethyl formamide, N-methylpyrrolidone; sulfoxides such as dimethyl sulfoxide; or chlorinated hydrocarbons such as dichloromethane, trichloromethane, or tetrachloroethane.

The reaction temperatures can vary within wide limits. Suitable temperatures are, for example, in the rage from −20° C. to the reflux temperature of the reaction mixture. It is preferred to carry out the reaction in the temperature range from 0° to 100° C. For the reaction to replace halogen by cyano (reaction b), higher temperatures are preferred, preferably in the range from 100° to 180° C.

The esterification reaction (d) can be carried out under especially mild conditions by using dicyclohexylcarbodiimide or the system diethyl azodicarboxylate/triphenylphosphine in diochloromethane or tetrahydrofuran, in the temperature range from 0° C. to room temperature. The esterification reaction (d) can also be carried out in accordance with customary laboratory practice using a dehydrating agent such as sulfuric acid, or by using catalytic amounts of a protonic acid in a water separator.

In general, the condensation reactions (a), (c) and (e) can be speeded up by addition of condensation catalysts and removing the reaction product ($H_2O$, HZ or HZ').

Particularly suitable catalysts, when using an aprotic solvent, are: p-toluenesulfonica acid, benzoic acid, sulfuric acid, hydrochloric acid or naphthalenesulfonic acid. Reactions of the above type are normally carried out for the preparation of carboxylic acid derivatives. They conform to general laboratory practice..

It is expedient to add a base in reaction (e). Examples of suitable bases are: sodium, potassium and calcium hydroxyide, alkali metal carbonates and alkaline earth metal carbonates, amines such as triethylamine or heterocyles such as pyridine, 4-dialkylaminopyridines, DABCO and alkali metal hydrides.

Reactions (b) and (e) can also be conveniently carried out under phase transfer conditions in two-phase systems. Such reactions are known to the skilled person and are described, for example, in Dehmlow and Dehmlow, Phase Transfer Catalysis, Verlag Chemie, Weinheim, 1983.

Although the synthesis of the final product, described in reaction (a), from a furandione II and an aniline III is operable in all circumstances, it can be useful for economic or technical reasons to convert specific compounds of formula I into other derivatives which fall under the scope of formula I. Exemplary of such conversions of specific compounds of formula I into other compunds of formula I is reaction (d). Furthermore, it is also possible to convert compounds of formula I, wherein $R^3$ or $R^4$ is, for example, haloalkyl or haloalkoxy, into compounds containing alkoxyalkyl, alkoxyalkoxy, aminoalkyl or aminoalkoxy radicals by reaction with alcohols or amines. Such conversion reactions are well-known to the skilled person.

The compounds of formulae II, V and VII are valuable intermediates for synthesising the compounds of the invention. The present invention therefore also relates to these intermediates in which $R^1$, $R^2$, X, Y, A and Z have the given meanings.

The intermediates III, V and VII are prepared by methods analogous to those known from the literature.

The anilines of formula IIIb, wherein A is $OR^4$, can be prepared in a three-step reaction in accordance with reaction scheme 1, starting from the known nitrobenzenes of formula XI (known e.g. from EP-A 61741, Chem. Ber. 59, 1254):

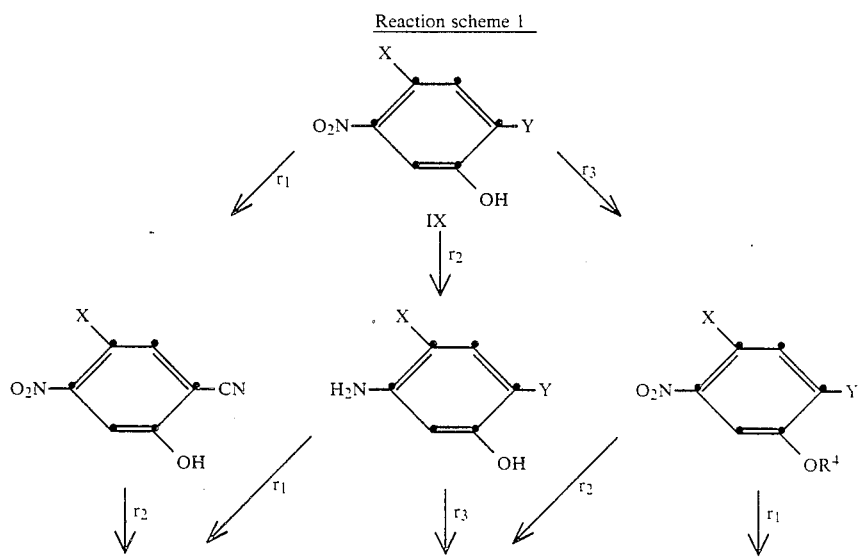

Reaction scheme 1

Reaction scheme 1

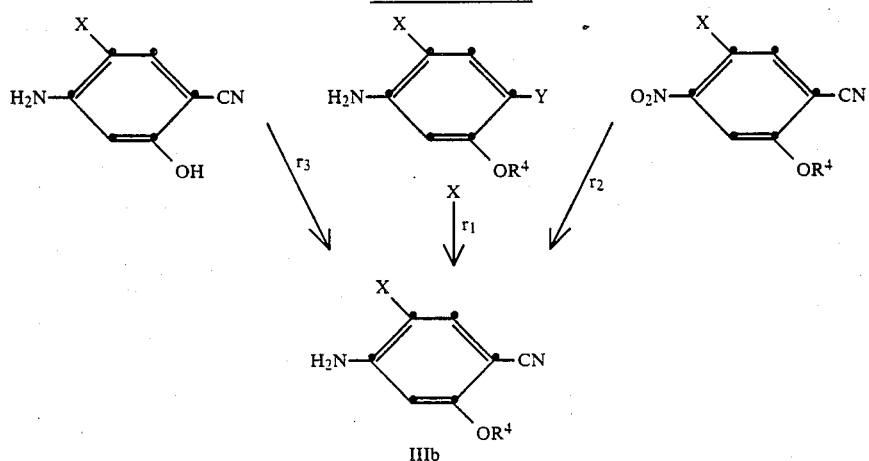

The necessary reaction steps $r_1$ (replacement of halogen by cyano), $r_2$ (reduction and $r_3$ (etherification) are known to the skilled person and can be carried out in accordance with methods known from the literature.

In like manner, the compounds of formula IIIa, wherein A is $COR^3$, can be prepared in accordance with reaction scheme 2 from the nitrobenzenes XI by replacement of halogen by cyano ($r_1$) and reduction ($r_2$)

N-phenylpyrrolidinedione obtainable from the furandione II and the aniline III ($r_1$) in the para-position at the phenyl ring ($r_2$), reduction ($r_3$) and subsequent diazotisation ($r_4$). The substituent Y can be introduced by subjecting the resultant diazonium salt to a Sandmeyer reaction ($r_4/r_5$), and then compounds of formula I prepared by replacement of halogen by cyano ($r_6$).

The process illustrated in reaction scheme 4 for the preparation of compounds of formula Ia, wherein A is

Reaction scheme 2

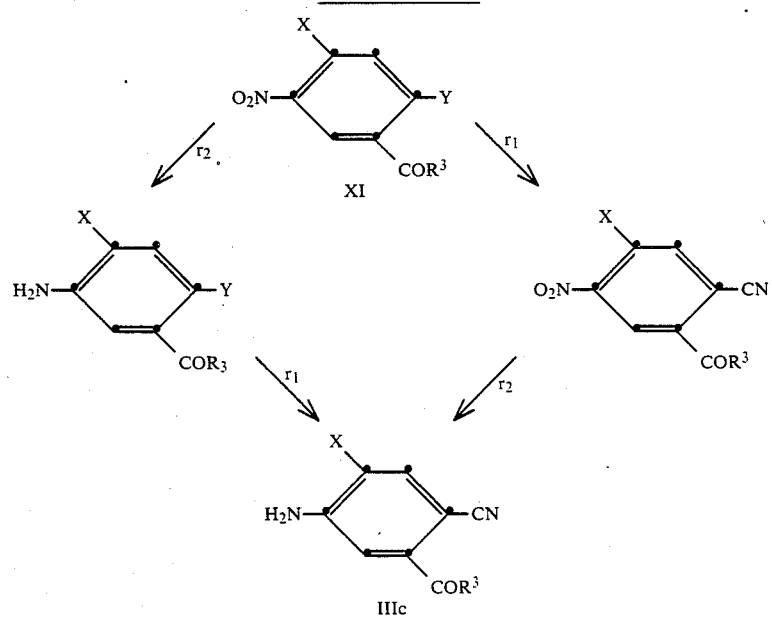

Reaction scheme 3 illustrates a further general means of preparing compounds of formula I by nitration of the $COR^4$, is also susceptible of broad application.

Reaction scheme 4
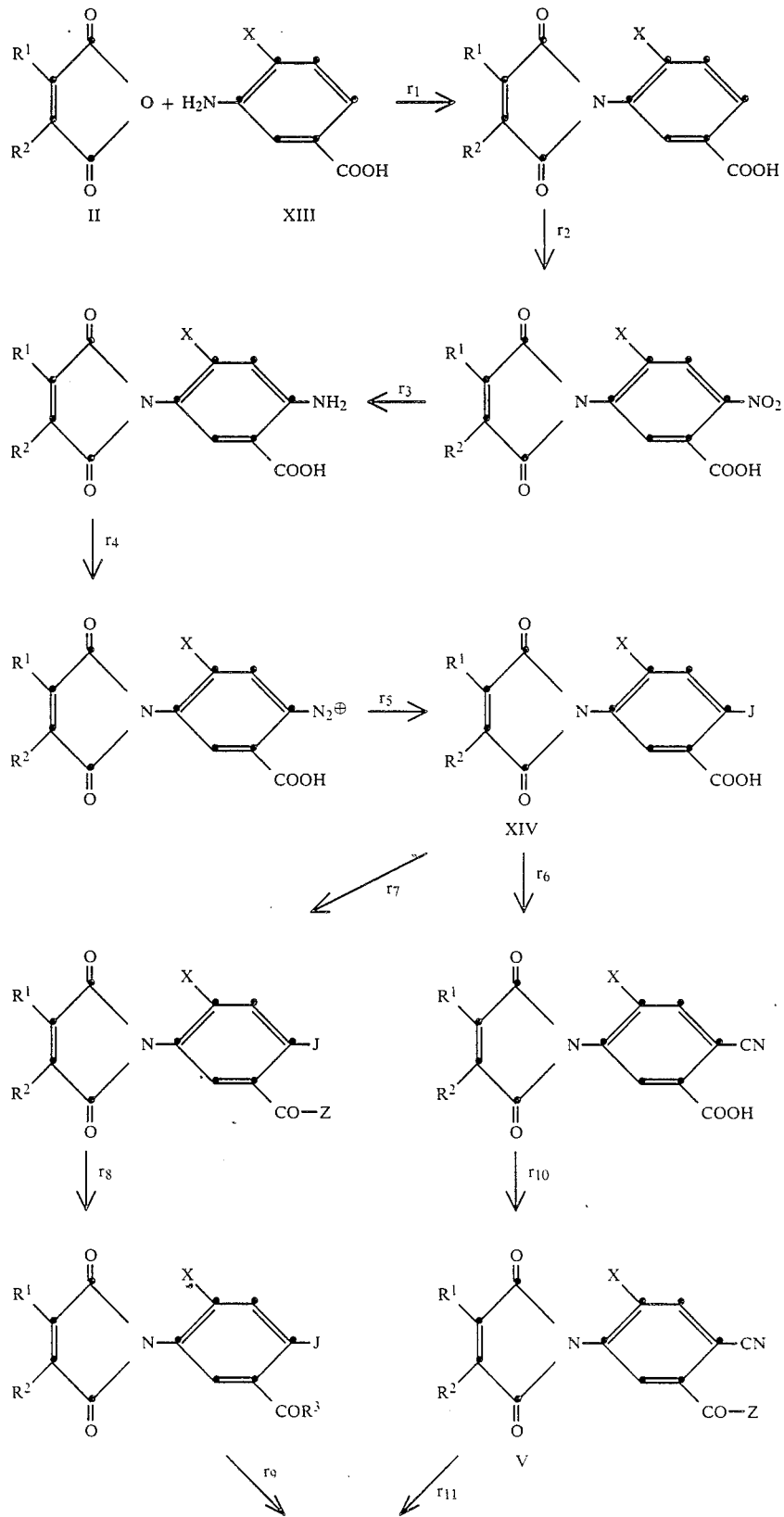

Reaction scheme 4
-continued

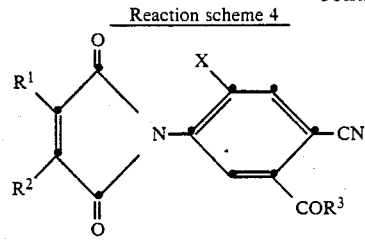

Process steps $r_1$ to $r_6$ in the above reaction scheme correspond to the reactions illustrated in reaction scheme 3, except that the iodine compound XIV is prepared first, starting from the m-anthranilic acid XIII also comprised by scheme 3.

Compound XIV can then be converted into an activated acid derivative ($r_7$) which is esterified ($r_8$) and then reacted to a compound Ia ($r_9$), or compound Ia is prepared by reversing the reactions steps by replacement of iodine by cyano ($r_6$), conversion into an activated acid derivative ($r_{10}$) and esterification ($r_{11}$).

The above reaction schemes 1 to 4 can also be used by analogy for the preparation of the intermediates III, V and VII (A or $OR^4$=CO—Z or OH).

The compounds of formula I are highly active herbicides which, when applied at suitable rates of application, are most suitable for use as selective herbicides for controlling weeds in crops of useful plants. Cultivated plants such as rye, barley, oats, corn, maize, sorghum, rice, cotton and soybeans remain almost undamaged at low rates of application. The growth of cultivated plants is affected to only an insignificant degree when the compounds of formula I are used in higher concentrations. When applied in very high concentrations, the compounds of formula I have total herbicidal properties.

The selective herbicidal activity of the compounds of this invention is observed in preemergence as well as postemergence application. These compounds can therefore be used very successfully for selective weed control when applied pre- and postemergence.

The compounds of this invention influence plant metabolism and can therefore also be used as growth regulators.

Previous experience with plant growth regulators has shown that they are able to induce one or more different responses in the plants. These different responses depend substantially on the time of application, based on the state of development of the seed or plant, as well as on the concentrations of active substance applied to the plants or to the locus thereof and on the mode of application. Growth regulators should at all events induce positive responses in the cultivated plants in the desired manner.

Influenced by growth regulators, the foliage of plants can be regulated in such a way that defoliation of the plants is achieved at a desired time. Such defoliation is useful for facilitating the mechanical harvesting of cotton, but is also of interest for facilitating the harvesting of other crops, e.g. in viticulture. defoliation can also be effected to diminish transpiration at a time when it is desired to transplant the plants.

It is also possible to control fruit drop with growth regulators. On the one hand premature fruit drop can be prevented and, on the other, fruit drop or even the fall of blossom can be promoted to a desired extent (thinning) in order to interrupt alternation. By alternation is meant the endogenic tendency of some kinds of fruit to give different yields from year to year. Finally, growth regulators can also be used for reducing the force necessary for detaching fruit at harvesting, so making possible mechanical harvesting of plants or facilitating manual harvesting.

The compounds of this invention, or the compositions containing them, can also be applied with advantage to the propagation parts of cultivated plants. To be singled out for special mention in this connection is seed dressing. Propagation parts are seeds, cuttings or other parts of the plant from which the cultivated plant can be reared. The present invention likewise relates to the propagation parts treated with a growth regulating or herbicidally effective amount of a compound of formula I.

The invention also relates to herbicidal and growth regulating compositions which contain a novel compound of formula I, and to methods of controlling weeds pre- and postemergence.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compounds of formula I and, where appropriate, a solid or liquid adjuvant, are prepared in known manner, e.g. by intimately mixing and/or grinding the active components with extenders, e.g. with solvents, solid carriers, and optionally surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybeam oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will be understood as comprising mixtures of surfactants.

Suitable anionic surfactants can be both water-soluble soaps and water-soluble synthetic surface-active compounds.

Suitable soaps are e.g. the alkali metal salts, alkaline earth metal salts or unsubstituted or substituted ammonium salts or high fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyl taurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfates and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamno-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl di(2-chloroethyl)ethylammonium bromide.

The surfactants customarily employed in the art of formulation are described e.g. in the following publications:

"1986 International McCutcheon's Detergents and Emulsifiers", Glen Rock, New Jersey, U.S.A.; Dr. Helmut Stache, "Tensid Taschenbuch" (Handbook of Surfactants), 2nd edition, Carl Hanser Verlag, Munich/Vienna 1981. M. and J. Ash "Encyclopedia of Surfactants", Vol. I–III, Chemical Publishing Co., New York, 1980-81.

The formulations of this invention usually contain 0.1 to 95%, preferably 0.1 to 80%, of a mixture of active components, 1 to 99.9%, of a solid or liquid adjuvant, and/or 0 to 25%, preferably 0.1 to 25%, of a surfactant.

Preferred formulations are composed in particular of the following constituents (%=percentage by weight):

| | |
|---|---|
| Emulsifiable concentrates | |
| compound of formula I: | 1 to 20%, preferably 5 to 10% |
| surfactant: | 5 to 30%, preferably 10 to 20% |
| liquid carrier: | 50 to 94%, preferably 70 to 85% |
| Dusts | |
| compound of formula I: | 0.1 to 10%, preferably 0.1 to 1% |
| solid carrier: | 99.9 to 90%, preferably 99.9 to 99% |
| Suspension concentrates | |
| compound of formula I: | 5 to 75%, preferably 10 to 50% |
| water: | 94 to 25%, preferably 88 to 30% |
| surfactant: | 1 to 40%, preferably 2 to 30% |
| Wettable powders | |
| compound of formula I: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| compound of formula I: | 0.5 to 30%, preferably 3 to 15% |
| solid carrier: | 99.5 to 70%, preferably 99 to 85%. |

Whereas commercial products will be preferably formulated as concentrates, the end user will normally employ dilute formulations. The formulations can be diluted to a concentration as low as 0.001% of active substance. The rates of application are usually from 0.001 to 4 kg a.s./ha, preferably from 0.005 to 1 kg a.s./ha.

The compositions may also contain further ingredients such as stabilisers, antiforms, viscosity regulators, binders, tackifiers, as well as fertilisers and other compounds for obtaining special effects.

The following Examples illustrate the invention.

EXAMPLE P 1.1

4-Cyano-2-fluoro-5-isopropoxynitrobenzene 375 g of 4-bromo-2-fluoro-5-isopropoxynitrobenzene are charged to 1 litre of dimethyl formamide. With stirring, 145 g of copper(I) cyanide are added and the mixture is slowly heated to 155° C. under argon. The reaction mixture begins to exotherm slightly at ca. 140° C. (the temperature of the reaction mixture rises to 153° C. and slowly subsides after ca. 45 minutes). The reaction mixture is thereafter stirred for 1 hour at 155° C. bath temperature and then cooled to room temperature. Insoluble deposit is removed by decantation and the reaction solution is concentrated by evaporation in a water jet vacuum. The oily residue is taken up in 1 litre of ethyl acetate and the solution is well stirred and decanted. The ethyl acetate solution is concentrated until the onset of crystallisation and cooled in ice-water. The precipitated product is filtered with suction, washed with ice-cold ethyl acetate, and dried. The same procedure is again carried out with the mother liquor.

The title compound of formula

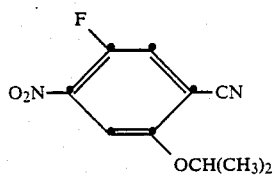

is isolated in a yield of 227 g in the form of a beige-coloured, flocculent powder which melts at 116°–118° C.

EXAMPLE P 1.2

4-Cyano-2-fluoro-5-isopropoxyaniline 160 g of tin(II) chloride . 2H₂O are charged to 184 ml of 37% hydrochloric acid. With stirring, 44 g of 4-cyano-2-fluoro-5-isopropoxynitrobenzene are added in portions to the colourless solution, whereupon an orange suspension forms. This suspension is slowly heated to reflux. A red solution forms at ca. 75° C. The reaction mixture is then stirred for 10 minutes at 110° C. bath temperature, cooled to room temperature, and then poured on to ca. 1.5 litres of ice-water. The pH is adjusted to 9 with concentrated sodium hydroxide solution. The resultant beige-coloured solution is extracted twice with ethyl acetate. The combined ethyl acetate phases are dried over magnesium sulfate, concentrated by evaporation under vacuum, and the residue is distilled under a high vacuum.

The title compound of formula

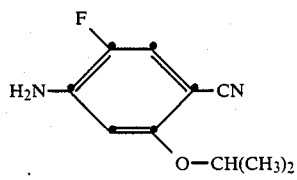

is obtained in a yield of 32.3 g in the form of a pale yellow oil with a boiling point of 143°–145° C. (10⁻² torr).

EXAMPLE P 1.3

2-(5-carboxy-2-fluoro-4-nitrophenyl)-4,5,6,7-tetrahydroisoindole-2H-1,3-dione 95 g of 2-(5-carboxy-2-fluorophenyl)-4,5,6,7-tetrahydroisoindole-2H-1,3-dione are added in portions of 5° C. to 75 ml of 96% sulfuric acid. With efficient stirring, 15 ml of 100% nitric acid are added dropwise to this mixture at the same temperature. Stirring is continued for 5 hours at room temperature and the reaction mixture is then poured on to ice. The precipitate is isolated by filtration, washed with cold water and dried, affording 98 g of the title compound of formula

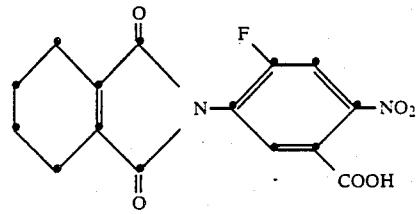

in the form of crystals which melt at 225°–227° C.

EXAMPLE P 1.4

2-4-amino-5-carboxy-2-fluorophenyl)-4,5,6,7-tetrahydroisoindole-2H-1,3-dione 71 g of 2-(5-carboxy-2-fluoro-4-nitrophenyl)-4,5,6,7-tetrahydroisoindole-2H-1,3-dione are hydrogenated with hydrogen under normal pressure in 720 ml of tetrahydrofuran at a temperature of 25°–30° C. in the presence of 14 g f Raney nickel. After the stoichiometric amount of hydrogen has been consumed, the catalyst is removed and the solution concentrated by evaporation, affording 54.6 g of the title compound of formula

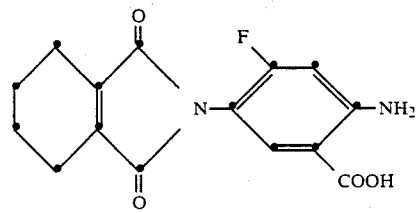

in the form of crystals which melt at 289° C.

EXAMPLE P 1.5

2-(5-carboxy-2-fluoro-4-iodophenyl)-4,5,6,7-tetrahydroisoindole-2H-1,3-dione

With stirring, 25 g of 2-(4-amino-5-carboxy-2-fluorophenyl)-4,5,6,7-tetrahydroisoindole-2H-1,3-d ione are added in portions to 100 ml of glacial acetic acid and 100 ml of 96% sulfuric acid, whereupon the temperature rises to 50° C. Stirring is continued until the educt is completely dissolved. The solution is then cooled to 5° C. and diazotised with a solution of 6.4 g of sodium nitrite in 40 ml of water. After stirring for a further 6 hours at room temperature, the diazotised product is added dropwise to a solution of 12.6 g of potassium iodide in 80 ml of water and stirring is continued for 1 hour at 40° C. The reaction mixture is poured on to ice-water, extracted with ethyl acetate, and the organic phase is washed with a solution of sodium bisulfite, dried, and concentrated by evaporation. Recrystallisation from methanol yields 25 g of the title compound of formula

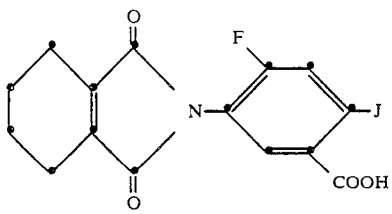

in the form of crystals which melt at 205°–207° C.

EXAMPLE P 2

1-(4-cyano-2-fluoro-5-isopropoxyphenyl)-3,4-dimethyl-pyrrole-1H-2,5-dione 8.9 g of 4-cyano-2-fluoro-5-isopropoxyaniline and 6.3 g of dimethylmaleic anhydride are heated to reflux in 50 ml of xylene in the presence of 1 g of 4-dimethylaminopyridine as catalyst. (With larger batches it is more advantageous to carry out the reaction in a water separator apparatus). The xylene is distilled off under a water jet vacuum and the residue is taken up in ethyl acetate and worked up on neutral substance. The organic phase is dried over sodium sulfate, the solvent is distilled off and the residue is recrystallised from ethanol, affording the title compound of formula

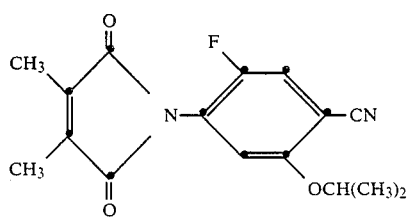

(compound 6.4)

in a yield of 7.1 g in the form of crystals which melt at 128°–132° C.

EXAMPLE P 3

2-(4-cyano-2-fluoro-5-isopropoxyphenyl)-4,5,6,7-tetrahydroisoindole-2H-1,3-dione 9.7 g of 4-cyano-2-fluoro-5-isopropoxyaniline and 7.6 g of 3,4,5,6-tetrahydrophthalic anhydride are refluxed in 300 ml of propionic acid for altogether 30 hours. After 16 hours, another 5 g of anhydride are added to bring the reaction to completion. The dark reaction mixture is left to stand for 2 days at room temperature and then the yellow precipitate formed during this time is isolatedd by suction filtration. This precipitate is recrystallised from toluene, affording 6.7 g of the title compound of formula

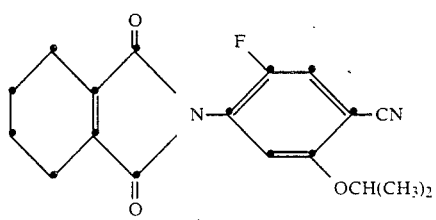

(compound 1.4)

in the form of crystals which melt at 138°–139° C. The crystals obtained from the recrystallisation from toluene contain about ⅓ mol of toluene in the crystal.

EXAMPLE P 4.1

2-(5-carboxy-4-cyano-2-fluorophenyl)-4,5,6,7-tetrahydroisoindole-2H-1,3-dione

A mixture of 4.2 g of 2-(5-carboxy-2-fluoro-4-iodophenyl)-4,5,6,7-tetrahydroisoindole-2H-1,3-dione and 0.9 g of copper(I) cyanide is refluxed for 14 hours in 50 ml of acetonitrile. After cooling, insoluble material is removed by suction filtration and the filtrate is concentrated to dryness, affording 2.7 g of the title compound of formula

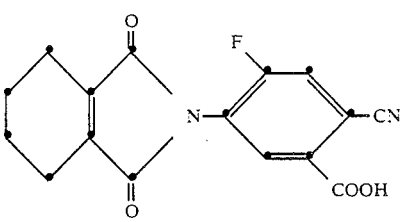

(compound 2.1)

in the form of crystals which melt at 203°–204° C.

EXAMPLE P 4.2

2-(5-chlorocarboxy-4-cyano-2-fluorophenyl)-4,5,6,7-tetrahydroisoindole-2H-1,3-dione 6 g of 2-(5-carboxy-4-cyano-2-fluorophenyl)-4,5,6,7-tetrahydroisoindole-2H-1,3-dione, 60 ml of thionyl chloride and 5 drops of dimethyl formamide are refluxed for 1 hour. The reaction mixture is then cooled and concentrated by evaporation under vacuum, affording 6 g of the title compound of formula

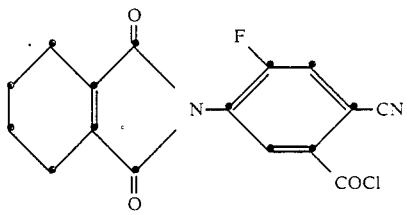

as viscous oil which can be used for subsequent reactions without further purification.

EXAMPLE P 4.3

2-(4-cyano-2-fluoro-5-isopropoxycarbonylphenyl)-4,5,6,7-tetrahydroisoindole-2H-1,3-dione A solution of 7.1 g of 2-(5-chlorocarbonyl-4-cyano-2-fluorophenyl)-4,5,6,7-tetrahydroisoindole-2H-1,3-dione in 50 ml of toluene is added dropwise at room temperature to a mixture of 5 ml of isopropanol, 5 ml of triethylamine and 50 ml of toluene, whereupon the temperature rises to 45° C. After stirring for 1 hour at room temperature, the triethylamine hydrochloride is separated and the filtrate is concentrated by evaporation, affording 5 g of the title compound of formula

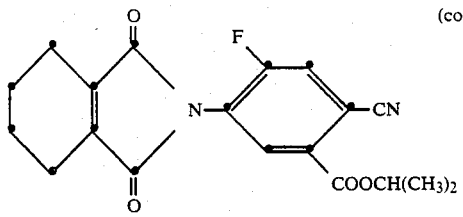

(compound 2.5)

in the form of crystals which melt at 173°–176° C.

EXAMPLE P 5.1

2-(5-chlorocarbonyl-2-fluoro-4-iodophenyl)-4,5,6,7-tetrahydroisoindole-2H-1,3-dione A mixture of 16.4 g of 2-(5-carboxy-2-fluoro-4-iodophenyl)-4,5,6,7-tetrahydroisoindole-2H-1,3-dione, 6 ml of thionyl chloride and 200 ml of toluene is heated to reflux for 12 hours. After cooling, the reaction mxiture is concentrated by evaporation under vacuum, affording 17.6 g of the title compound of formula

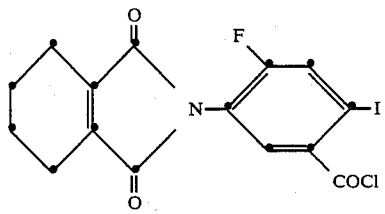

in the form of crystals which melt at 114°–117° C.

EXAMPLE P 5.2

2-(2-fluoro-4iodo-5-isopropoxycarbonylphenyl)-4,5,6,7-tetrahydroisoindole-2H-1,3-dione 17.1 g of 2-(5-chlorocarbonyl-2-fluoro-4-iodophenyl)-4,5,6,7-tetrahydroisoindole-2H-1,3-dione are added dropwise at room temperature to a mixture of 8 ml of isopropanol, 12 ml of triethylamine and 120 ml of toluene. After a reaction time of 12 hours, the precipitated triethylamine hydrochloride is removed and the filtrate is concentrated by evaporation, affording 7.2 g of the title compound of formula

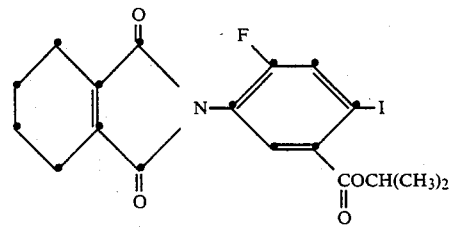

in the form of crystals which melt at 127°–132° C.

EXAMPLE P 5.3

2-(4-cyano-2-fluoro-5-isopropoxycarbonyl)-4,5,6,7-tetrahydroisoindole-2H-1,3-dione With stirring, a mixture of 2.3 g of 2-(2-fluoro-4-iodo-5-isopropoxycarbonylphenyl)-4,5,6,7-tetrahydroisoindole-2H-1,3-dione and 0.5 g of copper(I) cyanide is heated for 1 hour to 100° C. in 20 ml of dimethyl formamide. After cooling, the residue is removed by filtration and the filtrate is evaporated to dryness, affording 1.4 of the title compound of formula

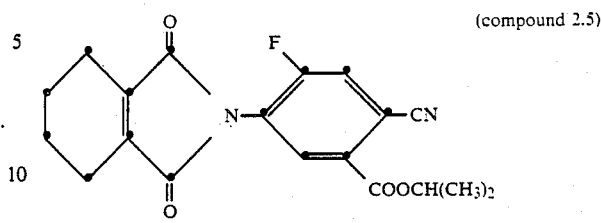

(compound 2.5)

in the form of crystals which melt at 173°–176° C.

The compounds listed in Tables 1 to 11 can be prepared in a manner corresponding to that described in Examples P2 to P5 above.

TABLE 1

Compounds of formula

| Comp. | X | $R^4$ | Phys. data |
|---|---|---|---|
| 1.1 | F | $CH_3$ | |
| 1.2 | F | $C_2H_5$ | |
| 1.3 | F | $C_3H_7$ | |
| 1.4 | F | $C_3H_7(i)$ | m.p: 138–139° C.* |
| 1.5 | F | $C_4H_9$ | |
| 1.6 | F | $C_4H_9(s)$ | |
| 1.7 | F | $C_4H_9(i)$ | |
| 1.8 | F | $C_4H_9(t)$ | |
| 1.9 | F | $-C_5H_{11}$ | |
| 1.10 | F | $-C_5H_{11}(s)$ | |
| 1.11 | F | $-CH_2-CH_2-OCH_3$ | |
| 1.12 | F | $-CH_2-CH=CH_2$ | |
| 1.13 | F | $-CH_2-CCl=CH_2$ | |
| 1.14 | F | $-CH_2-CH=CHCl$ | |
| 1.15 | F | $-CH_2-C\equiv CH$ | m.p: (196°) 200–202° |
| 1.16 | F | $-CH_2-C_6H_{11}$-(cycl.) | |
| 1.17 | F | $-CH_2-\text{(phenyl)}$ | |
| 1.18 | F | $-CH_2-COOCH_3$ | |
| 1.19 | F· | $-CH(CH_3)COOCH_3$ | |
| 1.20 | F | $-CH(CH_3)COOC_3H_7(i)$ | |
| 1.21 | F | $-CH(CH_3)COOC_4H_9(n)$ | |
| 1.22 | F | $-CH(CH_3)COSCH_3$ | |
| 1.23 | F | $-CH(CH_3)CONH_2$ | |
| 1.24 | F | $-CH(CH_3)CON(CH_3)_2$ | |
| 1.25 | F | $-COCH_3$ | |
| 1.26 | F | $-COC_6H_5$ | |
| 1.27 | F | $-CH(CH_3)-CH_2-S-CH_3$ | |
| 1.28 | F | $-CH(CH_3)-CH_2-S-CH(CH_3)_2$ | |
| 1.29 | F | $-CH_2-CH_2-OH$ | |

TABLE 1-continued

Compounds of formula

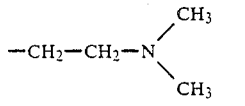

| Comp. | X | R⁴ | Phys. data |
|---|---|---|---|
| 1.30 | F | —CH₂—CH₂—Cl | |
| 1.31 | F | —CH₂—CN | |
| 1.32 | F | —CH₂—CH₂—N(CH₃)₂ | |
| 1.33 | F | —CH(CH₃)—CH₂—N(CH₃)₂ | |
| 1.34 | H | —CH₃ | |
| 1.35 | H | —C₂H₅ | |
| 1.36 | H | —C₃H₇ | |
| 1.37 | H | —C₃H₇(i) | |
| 1.38 | H | —C₄H₉(i) | |
| 1.39 | H | —C₄H₉(s) | |
| 1.40 | H | —CH₂—CH=CH₂ | |
| 1.41 | H | —CH₂—CCl=CH₂ | |
| 1.42 | H | —CH₂—CH=CHCl | |
| 1.43 | H | —CH₂—C≡CH | |
| 1.44 | H | —CH₂—COOCH₃ | |
| 1.45 | H | —CH(CH₃)COOCH₃ | |
| 1.46 | H | —CH(CH₃)—CH₂—S—CH₃ | |
| 1.47 | H | —CH(CH₃)—CH₂—S—C₂H₅ | |
| 1.48 | H | —CH(CH₃)—CH₂—S—C₃H₇(i) | |

*crystals contain about ¼ mol of toluene

TABLE 2

Compounds of formula

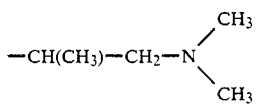

| Comp. | X | R³ | Phys. data |
|---|---|---|---|
| 2.1 | F | OH | m.p: 203–204° C. |
| 2.2 | F | OCH₃ | m.p: 136–141° C. |
| 2.3 | F | OC₂H₅ | m.p: 155–157° C. |
| 2.4 | F | OC₃H₇ | m.p: 86–90° C. |
| 2.5 | F | OC₃H₇(i) | m.p: 173–176° C. |
| 2.6 | F | OC₄H₉(n) | |
| 2.7 | F | OC₄H₉(i) | |
| 2.8 | F | OC₄H₉(s) | m.p: 80–82° C. |
| 2.9 | F | OC₄H₉(t) | |
| 2.10 | F | OC₅H₁₁ | |
| 2.11 | F | OC₅H₁₁(s) | |
| 2.12 | F | O—CH₂—CH₂—Cl | |
| 2.13 | F | O—CH₂—CH₂—OCH₃ | |
| 2.14 | F | O—CH₂—CH₂—O—C₂H₅ | |
| 2.15 | F | O—CH₂—CH₂—S—CH₃ | |
| 2.16 | F | O—CH₂(CH₃)—CH₂—S—CH₃ | |

TABLE 2-continued

Compounds of formula

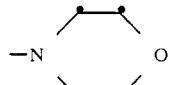

| Comp. | X | R³ | Phys. data |
|---|---|---|---|
| 2.17 | F | O—CH₂(CH₃)—CH₂—S—C₂H₅ | |
| 2.18 | F | O—CH₂(CH₃)—CH₂—S—C₃H₇(i) | |
| 2.19 | F | O—CH(CH₃)—CH₂—S—C₄H₉(n) | |
| 2.20 | F | O—CH₂(CH₃)—CH₂—S—C₄H₉(i) | |
| 2.21 | F | —O—CH₂—CH=CH₂ | |
| 2.22 | F | —O—CH₂—CCl=CH₂ | |
| 2.23 | F | —O—CH₂—CH=CHCl | |
| 2.24 | F | —OCH₂—C≡CH | |
| 2.25 | F | —O—CH₂—C₆H₁₁-(cycl.) | |
| 2.26 | F | —O—CH₂—C₃H₅-(cycl.) | |
| 2.27 | F | —O—CH₂—C₆H₅ | |
| 2.28 | F | —O—CH₂—COOCH₃ | |
| 2.29 | F | —O—CH(CH₃)COOCH₃ | |
| 2.30 | F | —O—CH(CH₃)COOC₂H₅ | |
| 2.31 | F | —O—CH(CH₃)COOC₃H₇i | |
| 2.32 | F | —O—CH(CH₃)COOC₄H₉(n) | |
| 2.33 | F | —O—CH(CH₃)COSCH₃ | |
| 2.34 | F | —O—CH(CH₃)CON(CH₃)₂ | |
| 2.35 | F | —S—CH₂—COOCH₃ | |
| 2.36 | F | —S—CH₂—COOC₂H₅ | |
| 2.37 | F | —S—CH(CH₃)—COOCH₃ | |
| 2.38 | F | —S—CH(CH₃)—COOC₂H₅ | |
| 2.39 | F | —S—CH(CH₃)—COOC₃H₇ | |
| 2.40 | F | —S—CH(CH₃)—COOC₃H₇(i) | |
| 2.41 | F | —SCH₃ | |
| 2.42 | F | —N(CH₃)₂ | |
| 2.43 | F | —N(CH₂—CH=CH₂)₂ | |
| 2.44 | F | 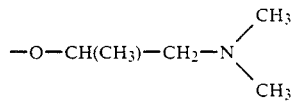 | |
| 2.45 | F | —O—CH(CH₃)—CH₂—N(CH₃)₂ | |
| 2.46 | H | —OH | |
| 2.47 | H | —OCH₃ | m.p.: (161°) 164–166° |
| 2.48 | H | —OC₂H₅ | |
| 2.49 | H | OC₃H₇(n) | |
| 2.50 | H | OC₃H₇(i) | |
| 2.51 | H | OC₄H₉(i) | |
| 2.52 | H | OC₄H₉(s) | |
| 2.53 | H | OCH₂—CH=CH₂ | |
| 2.54 | H | OCH₂—CCl=CH₂ | |
| 2.55 | H | OCH₂—CH=CHCl | |
| 2.56 | H | —OCH₂—C≡CH | |
| 2.57 | H | —OCH₂—COOCH₃ | |
| 2.58 | H | —OCH(CH₃)COOCH₃ | |
| 2.59 | H | —OCH(CH₃)CH₂—S—CH₃ | |
| 2.60 | H | —OCH(CH₃)CH₂—S—C₂H₅ | |
| 2.61 | H | —OCH(CH₃)CH₂—S—C₃H₇i | |
| 2.62 | H | —S—CH₂—COOCH₃ | |
| 2.63 | H | —S—CH₂—COOC₂H₅ | |
| 2.64 | H | —S—CH(CH₃)COOCH₃ | |
| 2.65 | H | —S—CH(CH₃)COOC₂H₅ | |
| 2.66 | H | —S—CH(CH₃)—COO—C₃H-i | |

TABLE 3

Compounds of formula

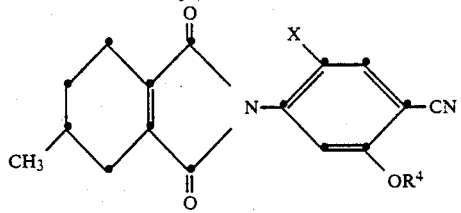

| Comp. | X | R⁴ | Phys. data |
|---|---|---|---|
| 3.1 | F | CH₃ | |
| 3.2 | F | C₃H₇i | m.p: 147–149° C. |
| 3.3 | F | CH₂—CH=CH₂ | |
| 3.4 | F | CH₂—CCl=CH₂ | |
| 3.5 | F | CH₂—CH=CHCl | |
| 3.6 | F | CH₂—C≡CH | |
| 3.7 | F | —CH₂—COOCH₃ | |
| 3.8 | F | —CH(CH₃)—COOCH₃ | |

TABLE 4

Compounds of formula

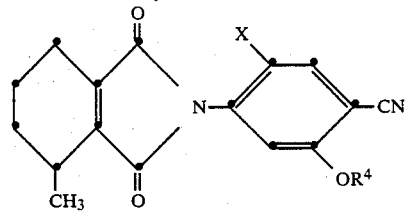

| Comp. | X | R⁴ | Phys. data |
|---|---|---|---|
| 4.1 | F | CH₃ | |
| 4.2 | F | C₃H₇i | |
| 4.3 | F | —CH₂—CH=CH₂ | |
| 4.4 | F | —CH₂—CCl=CH₂ | |
| 4.5 | F | —CH₂—CH=CHCl | |
| 4.6 | F | —CH₂—C≡CH | |
| 4.7 | F | —CH₂—COOCH₃ | |
| 4.8 | F | —CH₂(CH₃)COOCH₃ | |

TABLE 5

Compounds of formula

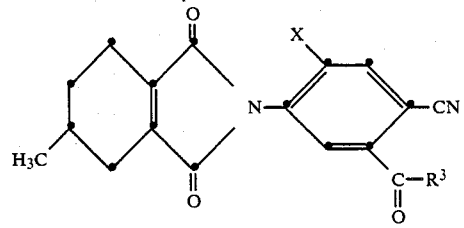

| Comp. | X | R³ | Phys. data |
|---|---|---|---|
| 5.1 | F | OCH₃ | |
| 5.2 | F | OC₂H₅ | |
| 5.3 | F | OC₃H₇(i) | |
| 5.4 | F | OC₄H₉(i) | |
| 5.5 | F | OCH₂—CH₂—Cl | |
| 5.6 | F | OCH₂—COOCH₃ | |
| 5.7 | F | OCH₂—COOC₂H₅ | |
| 5.8 | F | OCH(CH₃)—COOCH₃ | |
| 5.9 | F | S—CH₂—COOCH₃ | |
| 5.10 | F | —S—CH₂—COOC₂H₅ | |
| 5.11 | F | —S—CH(CH₃)COOCH₃ | |
| 5.12 | F | —S—CH(CH₃)COOC₃H₇(i) | |
| 5.13 | F | —O—CH(CH₃)—CH₂—S—CH₃ | |

TABLE 6

Compounds of formula

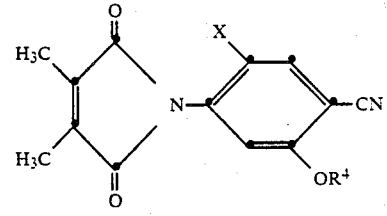

| Comp. | X | R⁴ | Phys. data |
|---|---|---|---|
| 6.1 | F | CH₃ | |
| 6.2 | F | C₂H₅ | |
| 6.3 | F | C₃H₇ | |
| 6.4 | F | C₃H₇(i) | m.p.: 128–132° C. |
| 6.5 | F | C₄H₉ | |
| 6.6 | F | C₄H₉(s) | |
| 6.7 | F | C₄H₉(i) | |
| 6.8 | F | C₄H₉(t) | |
| 6.9 | F | —C₅H₁₁ | |
| 6.10 | F | —C₅H₁₁(s) | |
| 6.11 | F | —CH₂—CH₂—OCH₃ | |
| 6.12 | F | —CH₂—CH=CH₂ | |
| 6.13 | F | —CH₂—CCl=CH₂ | |
| 6.14 | F | —CH₂—CH=CHCl | |
| 6.15 | F | —CH₂—C≡CH | |
| 6.16 | F | —CH₂—C₆H₁₁-(cycl.) | |
| 6.17 | F | —CH₂—C₆H₅ (phenyl) | |
| 6.18 | F | —CH₂—COOCH₃ | |
| 6.19 | F | —CH(CH₃)COOCH₃ | |
| 6.20 | F | —CH(CH₃)COOC₃H₇(i) | |
| 6.21 | F | —CH(CH₃)COOC₄H₉(n) | |
| 6.22 | F | —CH(CH₃)COSCH₃ | |
| 6.23 | F | —CH(CH₃)CONH₂ | |
| 6.24 | F | —CH(CH₃)CON(CH₃)₂ | |
| 6.25 | F | —COCH₃ | |
| 6.26 | F | —COC₆H₅ | |
| 6.27 | F | —CH(CH₃)—CH₂—S—CH₃ | |
| 6.28 | F | —CH(CH₃)—CH₂—S—CH(CH₃)₂ | |
| 6.29 | F | —CH₂—CH₂—OH | |
| 6.30 | F | —CH₂—CH₂—Cl | |
| 6.31 | F | —CH₂—CN | |
| 6.32 | F | —CH₂—CH₂—N(CH₃)₂ | |
| 6.33 | F | —CH(CH₃)—CH₂—N(CH₃)₂ | |
| 6.34 | H | —CH₃ | |
| 6.35 | H | —C₂H₅ | |
| 6.36 | H | —C₃H₇ | |
| 6.37 | H | —C₃H₇(i) | |
| 6.38 | H | —C₄H₉(i) | |
| 6.39 | H | —C₄H₉(s) | |
| 6.40 | H | —CH₂—CH=CH₂ | |

TABLE 6-continued

Compounds of formula

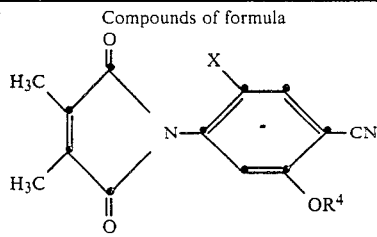

| Comp. | X | R⁴ | Phys. data |
|---|---|---|---|
| 6.41 | H | —CH₂—CCl=CH₂ | |
| 6.42 | H | —CH₂—CH=CHCl | |
| 6.43 | H | —CH₂—C≡CH | |
| 6.44 | H | —CH₂—COOCH₃ | |
| 6.45 | H | —CH(CH₃)COOCH₃ | |
| 6.46 | H | —CH(CH₃)—CH₂—S—CH₃ | |
| 6.47 | H | —CH(CH₃)—CH₂—S—C₂H₅ | |

TABLE 7

Compounds of formula

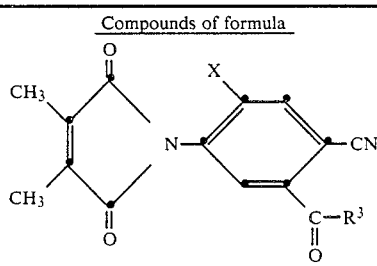

| Comp. | X | R³ | Phys. data |
|---|---|---|---|
| 7.1 | F | OH | |
| 7.2 | F | OCH₃ | |
| 7.3 | F | OC₂H₅ | |
| 7.4 | F | OC₃H₇ | |
| 7.5 | F | OC₃H₇(i) | |
| 7.6 | F | OC₄H₉(n) | |
| 7.7. | F | OC₄H₉(i) | |
| 7.8 | F | OC₄H₉(s) | |
| 7.9 | F | OC₄H₉(t) | |
| 7.10 | F | OC₅H₁₁ | |
| 7.11 | F | OC₅H₁₁(s) | |
| 7.12 | F | O—CH₂—CH₂—Cl | |
| 7.13 | F | O—CH₂—CH₂—OCH₃ | |
| 7.14 | F | O—CH₂—CH₂—O—C₂H₅ | |
| 7.15 | F | O—CH₂—CH₂—S—CH₃ | |
| 7.16 | F | O—CH₂(CH₃)—CH₂—S—CH₃ | |
| 7.17 | F | O—CH₂(CH₃)—CH₂—S—C₂H₅ | |
| 7.18 | F | O—CH₂(CH₃)—CH₂—S—C₃H₇(i) | |
| 7.19 | F | O—CH(CH₃)—CH₂—S—C₄H₉(n) | |
| 7.20 | F | O—CH₂(CH₃)—CH₂—S—C₄H₉(i) | |
| 7.21 | F | —O—CH₂—CH=CH₂ | |
| 7.22 | F | —O—CH₂—CCl=CH₂ | |
| 7.23 | F | —O—CH₂—CH=CHCl | |
| 7.24 | F | —OCH₂—C≡CH | |
| 7.25 | F | —O—CH₂—C₆H₁₁-(cycl.) | |
| 7.26 | F | —O—CH₂—C₃H₅-(cycl.) | |
| 7.27 | F | —O—CH₂—C₆H₅ | |
| 7.28 | F | —O—CH₂—COOCH₃ | |
| 7.29 | F | —O—CH(CH₃)COOCH₃ | |
| 7.30 | F | —O—CH(CH₃)COOC₂H₅ | |
| 7.31 | F | —O—CH(CH₃)COOC₃H₇(i) | |
| 7.32 | F | —O—CH(CH₃)COOC₄H₉(n) | |
| 7.33 | F | —O—CH(CH₃)COSCH₃ | |
| 7.34 | F | —O—CH(CH₃)CON(CH₃)₂ | |
| 7.35 | F | —S—CH₂—COOCH₃ | |
| 7.36 | F | —S—CH₂—COOC₂H₅ | |
| 7.37 | F | —S—CH(CH₃)—COOCH₃ | |
| 7.38 | F | —S—CH(CH₃)—COOC₂H₅ | |
| 7.39 | F | —S—CH(CH₃)—COOC₃H₇ | |
| 7.40 | F | —S—CH(CH₃)—COOC₃H₇(i) | |
| 7.41 | F | —SCH₃ | |
| 7.42 | F | —N(CH₃)₂ | |
| 7.43 | F | —N(CH₂—CH=CH₂)₂ | |

TABLE 7-continued

Compounds of formula

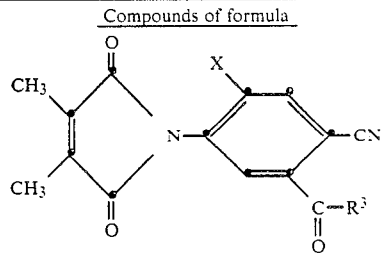

| Comp. | X | R³ | Phys. data |
|---|---|---|---|
| 7.44 | F | —N⟨morpholino⟩ | |
| 7.45 | F | —O—CH(CH₃)—CH₂—N(CH₃)₂ | |
| 7.46 | H | —OH | |
| 7.47 | H | —OCH₃ | |
| 7.48 | H | —OC₂H₅ | |
| 7.49 | H | OC₃H₇(n) | |
| 7.50 | H | OC₃H₇(i) | |
| 7.51 | H | OC₄H₉(i) | |
| 7.52 | H | OC₄H₉(s) | |
| 7.53 | H | OCH₂—CH=CH₂ | |
| 7.54 | H | OCH₂—CCl=CH₂ | |
| 7.55 | H | OCH₂—CH=CHCl | |
| 7.56 | H | —OCH₂—C≡CH | |
| 7.57 | H | —OCH₂—COOCH₃ | |
| 7.58 | H | —OCH(CH₃)COOCH₃ | |
| 7.59 | H | —OCH(CH₃)CH₂—S—CH₃ | |
| 7.60 | H | —OCH(CH₃)CH₂—S—C₂H₅ | |
| 7.61 | H | —OCH(CH₃)CH₂—S—C₃H₇(i) | |
| 7.62 | H | —S—CH₂—COOCH₃ | |
| 7.63 | H | —S—CH₂—COOC₂H₅ | |
| 7.64 | H | —S—CH(CH₃)COOCH₃ | |
| 7.65 | H | —S—CH(CH₃)COOC₂H₅ | |
| 7.66 | H | —S—CH(CH₃)—COO—C₃H₇(i) | |

TABLE 8

Compounds of formula

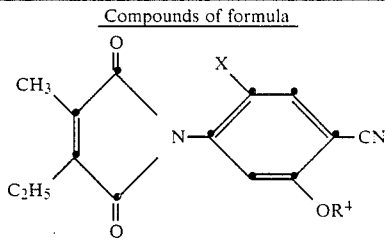

| Comp. | X | R⁴ | Phys. data |
|---|---|---|---|
| 8.1 | F | CH₃ | |
| 8.2 | F | C₂H₅ | |
| 8.3 | F | C₃H₇ | |
| 8.4 | F | C₃H₇(i) | m.p.: 98-100° C. |
| 8.5 | F | C₄H₉ | |
| 8.6 | F | C₄H₉(s) | |
| 8.7 | F | C₄H₉(i) | |
| 8.8 | F | C₄H₉(t) | |
| 8.9 | F | —C₅H₁₁ | |
| 8.10 | F | —C₅H₁₁(s) | |
| 8.11 | F | —CH₂—CH₂—OCH₃ | |
| 8.12 | F | —CH₂—CH=CH₂ | |
| 8.13 | F | —CH₂—CCl=CH₂ | |
| 8.14 | F | —CH₂—CH=CHCl | |
| 8.15 | F | —CH₂—C≡CH | |
| 8.16 | F | —CH₂—C₆H₁₁-(cycl.) | |

TABLE 8-continued

Compounds of formula

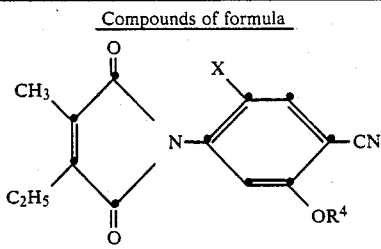

| Comp. | X | R⁴ | Phys. data |
|---|---|---|---|
| 8.17 | F | —CH₂—C₆H₅ (phenyl) | |
| 8.18 | F | —CH₂—COOCH₃ | |
| 8.19 | F | —CH(CH₃)COOCH₃ | |
| 8.20 | F | —CH(CH₃)COOC₃H₇(i) | |
| 8.21 | F | —CH(CH₃)COOC₄H₉(n) | |
| 8.22 | F | —CH(CH₃)COSCH₃ | |
| 8.23 | F | —CH(CH₃)CONH₂ | |
| 8.24 | F | —CH(CH₃)CON(CH₃)₂ | |
| 8.25 | F | —COCH₃ | |
| 8.26 | F | —COC₆H₅ | |
| 8.27 | F | —CH(CH₃)—CH₂—S—CH₃ | |
| 8.28 | F | —CH(CH₃)—CH₂—S—CH(CH₃)₂ | |
| 8.29 | F | —CH₂—CH₂—OH | |
| 8.30 | F | —CH₂—CH₂—Cl | |
| 8.31 | F | —CH₂—CN | |
| 8.32 | F | —CH₂—CH₂—N(CH₃)₂ | |
| 8.33 | F | —CH(CH₃)—CH₂—N(CH₃)₂ | |
| 8.34 | H | —CH₃ | |
| 8.35 | H | —C₂H₅ | |
| 8.36 | H | —C₃H₇ | |
| 8.47 | H | —C₃H₇(i) | |
| 8.38 | H | —C₄H₉(i) | |
| 8.39 | H | —C₄H₉(s) | |
| 8.40 | H | —CH₂—CH=CH₂ | |
| 8.41 | H | —CH₂—CCl=CH₂ | |
| 8.42 | H | —CH₂—CH=CHCl | |
| 8.43 | H | —CH₂—C≡CH | |
| 8.44 | H | —CH₂—COOCH₃ | |
| 8.45 | H | —CH(CH₃)COOCH₃ | |
| 8.46 | H | —CH(CH₃)—CH₂—S—CH₃ | |
| 8.47 | H | —CH(CH₃)—CH₂—S—C₂H₅ | |
| 8.48 | H | —CH(CH₃)—CH₂—S—C₃H₇(i) | |

TABLE 9

Compounds of formula

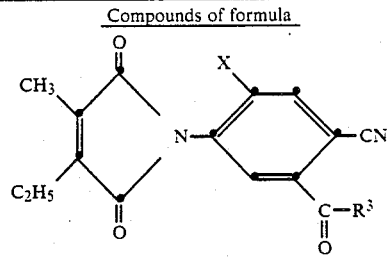

| Comp. | X | R³ | Phys. data |
|---|---|---|---|
| 9.1 | F | OH | |
| 9.2 | F | OCH₃ | |
| 9.3 | F | OC₂H₅ | |
| 9.4 | F | OC₃H₇ | |
| 9.5 | F | OC₃H₇(i) | |
| 9.6 | F | OC₄H₉(n) | |
| 9.7. | F | OC₄H₉(i) | |
| 9.8 | F | OC₄H₉(s) | |
| 9.9 | F | OC₄H₉(t) | |
| 9.10 | F | OC₅H₁₁ | |
| 9.11 | F | OC₅H₁₁(s) | |
| 9.12 | F | O—CH₂—CH₂—Cl | |
| 9.13 | F | O—CH₂—CH₂—OCH₃ | |
| 9.14 | F | O—CH₂—CH₂—O—C₂H₅ | |
| 9.15 | F | O—CH₂—CH₂—S—CH₃ | |
| 9.16 | F | O—CH₂(CH₃)—CH₂—S—CH₃ | |
| 9.17 | F | O—CH₂(CH₃)—CH₂—S—C₂H₅ | |
| 9.18 | F | O—CH₂(CH₃)—CH₂—S—C₃H₇(i) | |
| 9.19 | F | O—CH(CH₃)—CH₂—S—C₄H₉(n) | |
| 9.20 | F | O—CH₂(CH₃)—CH₂—S—C₄H₉(i) | |
| 9.21 | F | —O—CH₂—CH=CH₂ | |
| 9.22 | F | —O—CH₂—CCl=CH₂ | |
| 9.23 | F | —O—CH₂—CH=CHCl | |
| 9.24 | F | —OCH₂—C≡CH | |
| 9.25 | F | —O—CH₂—C₆H₁₁-(cycl.) | |
| 9.26 | F | —O—CH₂—C₃H₅-(cycl.) | |
| 9.27 | F | —O—CH₂—C₆H₅ | |
| 9.28 | F | —O—CH₂—COOCH₃ | |
| 9.29 | F | —O—CH(CH₃)COOCH₃ | |
| 9.30 | F | —O—CH(CH₃)COOC₂H₅ | |
| 9.31 | F | —O—CH(CH₃)COOC₃H₇(i) | |
| 9.32 | F | —O—CH(CH₃)COOC₄H₉(n) | |
| 9.33 | F | —O—CH(CH₃)COSCH₃ | |
| 9.34 | F | —O—CH(CH₃)CON(CH₃)₂ | |
| 9.35 | F | —S—CH₂—COOCH₃ | |
| 9.36 | F | —S—CH₂—COOC₂H₅ | |
| 9.37 | F | —S—CH(CH₃)—COOCH₃ | |
| 9.38 | F | —S—CH(CH₃)—COOC₂H₅ | |
| 9.39 | F | —S—CH(CH₃)—COOC₃H₇ | |
| 9.40 | F | —S—CH(CH₃)—COOC₃H₇(i) | |
| 9.41 | F | —SCH₃ | |
| 9.42 | F | —N(CH₃)₂ | |
| 9.43 | F | —N(CH₂—CH=CH₂)₂ | |
| 9.44 | F | —N(morpholino) (—N\_\_O ring) | |
| 9.45 | F | —O—CH(CH₃)—CH₂—N(CH₃)₂ | |
| 9.46 | H | —OH | |
| 9.47 | H | —OCH₃ | |
| 9.48 | H | —OC₂H₅ | |
| 9.49 | H | OC₃H₇(n) | |
| 9.50 | H | OC₃H₇(i) | |
| 9.51 | H | OC₄H₉(i) | |
| 9.52 | H | OC₄H₉(s) | |
| 9.53 | H | OCH₂—CH=CH₂ | |
| 9.54 | H | OCH₂—CCl=CH₂ | |
| 9.55 | H | OCH₂—CH=CHCl | |
| 9.56 | H | —OCH₂—C≡CH | |
| 9.57 | H | —OCH₂—COOCH₃ | |

TABLE 9-continued

Compounds of formula (with CH₃, C₂H₅ substituents on dione ring, X on pyridine, CN, C(=O)R³)

| Comp. | X | R³ | Phys. data |
|---|---|---|---|
| 9.58 | H | —OCH(CH₃)COOCH₃ | |
| 9.59 | H | —OCH(CH₃)CH₂—S—CH₃ | |
| 9.60 | H | —OCH(CH₃)CH₂—S—C₂H₅ | |
| 9.61 | H | —OCH(CH₃)CH₂—S—C₃H₇(i) | |
| 9.62 | H | —S—CH₂—COOCH₃ | |
| 9.63 | H | —S—CH₂—COOC₂H₅ | |
| 9.64 | H | —S—CH(CH₃)COOCH₃ | |
| 9.65 | H | —S—CH(CH₃)COOC₂H₅ | |
| 9.66 | H | —S—CH(CH₃)—COO—C₃H₇(i) | |

TABLE 10

Compounds of formula (with C₂H₅, C₂H₅ substituents on dione ring, X on pyridine, CN, OR⁴)

| Comp. | X | R⁴ | Phys. data |
|---|---|---|---|
| 10.1 | F | CH₃ | |
| 10.2 | F | C₂H₅ | |
| 10.3 | F | C₃H₇ | |
| 10.4 | F | C₃H₇(i) | |
| 10.5 | F | C₄H₉ | |
| 10.6 | F | C₄H₉(s) | |
| 10.7 | F | C₄H₉(i) | |
| 10.8 | F | C₄H₉(t) | |
| 10.9 | F | —C₅H₁₁ | |
| 10.10 | F | —C₅H₁₁(s) | |
| 10.11 | F | —CH₂—CH₂—OCH₃ | |
| 10.12 | F | —CH₂—CH=CH₂ | |
| 10.13 | F | —CH₂—CCl=CH₂ | |
| 10.14 | F | —CH₂—CH=CHCl | |
| 10.15 | F | —CH₂—C≡CH | |
| 10.16 | F | —CH₂—C₆H₁₁-(cycl.) | |
| 10.17 | F | —CH₂—C₆H₅ | |
| 10.18 | F | —CH₂—COOCH₃ | |
| 10.19 | F | —CH(CH₃)COOCH₃ | |
| 10.20 | F | —CH(CH₃)COOC₃H₇(i) | |
| 10.21 | F | —CH(CH₃)COOC₄H₉(n) | |
| 10.22 | F | —CH(CH₃)COSCH₃ | |
| 10.23 | F | —CH(CH₃)CONH₂ | |
| 10.24 | F | —CH(CH₃)CON(CH₃)₂ | |
| 10.25 | F | —COCH₃ | |
| 10.26 | F | —COC₆H₅ | |
| 10.27 | F | —CH(CH₃)—CH₂—S—CH₃ | |
| 10.28 | F | —CH(CH₃)—CH₂—S—CH(CH₃)₂ | |
| 10.29 | F | —CH₂—CH₂—OH | |
| 10.30 | F | —CH₂—CH₂—Cl | |
| 10.31 | F | —CH₂—CN | |
| 10.32 | F | —CH₂—CH₂—N(CH₃)₂ | |
| 10.33 | F | —CH(CH₃)—CH₂—N(CH₃)₂ | |
| 10.34 | H | —CH₃ | |
| 10.35 | H | —C₂H₅ | |
| 10.36 | H | —C₃H₇ | |
| 10.37 | H | —C₃H₇(i) | |
| 10.38 | H | —C₄H₉(i) | |
| 10.39 | H | —C₄H₉(s) | |
| 10.40 | H | —CH₂—CH=CH₂ | |
| 10.41 | H | —CH₂—CCl=CH₂ | |
| 10.42 | H | —CH₂—CH=CHCl | |
| 10.43 | H | —CH₂—C≡CH | |
| 10.44 | H | —CH₂—COOCH₃ | |
| 10.45 | H | —CH(CH₃)COOCH₃ | |
| 10.46 | H | —CH(CH₃)—CH₂—S—CH₃ | |
| 10.47 | H | —CH(CH₃)—CH₂—S—C₂H₅ | |
| 10.48 | H | —CH(CH₃)—CH₂—S—C₃H₇(i) | |

TABLE 11

Compounds of formula (with C₂H₅, C₂H₅ substituents on dione ring, X on pyridine, CN, C(=O)R³)

| Comp. | X | R³ | Phys. data |
|---|---|---|---|
| 11.1 | F | OH | |
| 11.2 | F | OCH₃ | |
| 11.3 | F | OC₂H₅ | |
| 11.4 | F | OC₃H₇ | |
| 11.5 | F | OC₃H₇(i) | |
| 11.6 | F | OC₄H₉(n) | |
| 11.7 | F | OC₄H₉(i) | |
| 11.8 | F | OC₄H₉(s) | |
| 11.9 | F | OC₄H₉(t) | |
| 11.10 | F | OC₅H₁₁ | |
| 11.11 | F | OC₅H₁₁(s) | |
| 11.12 | F | O—CH₂—CH₂—Cl | |
| 11.13 | F | O—CH₂—CH₂—OCH₃ | |
| 11.14 | F | O—CH₂—CH₂—O—C₂H₅ | |

TABLE 11-continued

Compounds of formula

[Structure: diethyl-substituted dioxo-pyrrolidine N-linked to phenyl ring bearing X, CN, and C(=O)-R³ substituents]

| Comp. | X | R³ | Phys. data |
|---|---|---|---|
| 11.15 | F | O—CH₂—CH₂—S—CH₃ | |
| 11.16 | F | O—CH₂(CH₃)—CH₂—S—CH₃ | |
| 11.17 | F | O—CH₂(CH₃)—CH₂—S—C₂H₅ | |
| 11.18 | F | O—CH₂(CH₃)—CH₂—S—C₃H₇(i) | |
| 11.19 | F | O—CH(CH₃)—CH₂—S—C₄H₉(n) | |
| 11.20 | F | O—CH₂(CH₃)—CH₂—S—C₄H₉(i) | |
| 11.21 | F | —O—CH₂—CH=CH₂ | |
| 11.22 | F | —O—CH₂—CCl=CH₂ | |
| 11.23 | F | —O—CH₂—CH=CHCl | |
| 11.24 | F | —OCH₂—C≡CH | |
| 11.25 | F | —O—CH₂—C₆H₁₁-(cycl.) | |
| 11.26 | F | —O—CH₂—C₃H₅-(cycl.) | |
| 11.27 | F | —O—CH₂—C₆H₅ | |
| 11.28 | F | —O—CH₂—COOCH₃ | |
| 11.29 | F | —O—CH(CH₃)COOCH₃ | |
| 11.30 | F | —O—CH(CH₃)COOC₂H₅ | |
| 11.31 | F | —O—CH(CH₃)COOC₃H₇(i) | |
| 11.32 | F | —O—CH(CH₃)COOC₄H₉(n) | |
| 11.33 | F | —O—CH(CH₃)COSCH₃ | |
| 11.34 | F | —O—CH(CH₃)CON(CH₃)₂ | |
| 11.35 | F | —S—CH₂—COOCH₃ | |
| 11.36 | F | —S—CH₂—COOC₂H₅ | |
| 11.37 | F | —S—CH(CH₃)—COOCH₃ | |
| 11.38 | F | —S—CH(CH₃)—COOC₂H₅ | |
| 11.39 | F | —S—CH(CH₃)—COOC₃H₇ | |
| 11.40 | F | —S—CH(CH₃)—COOC₃H₇(i) | |
| 11.41 | F | —SCF₃ | |
| 11.42 | F | —N(CH₃)₂ | |
| 11.43 | F | —N(CH₂—CH=CH₂)₂ | |
| 11.44 | F | —N(morpholino ring) | |
| 11.45 | F | —O—CH(CH₃)—CH₂—N(CH₃)₂ | |
| 11.46 | H | —OH | |
| 11.47 | H | —OCH₃ | |
| 11.48 | H | —OC₂H₅ | |
| 11.49 | H | OC₃H₇(n) | |
| 11.50 | H | OC₃H₇(i) | |
| 11.51 | H | OC₄H₉(i) | |
| 11.52 | H | OC₄H₉(s) | |
| 11.53 | H | OCH₂—CH=CH₂ | |
| 11.54 | H | OCH₂—CCl=CH₂ | |
| 11.55 | H | OCH₂—CH=CHCl | |
| 11.56 | H | —OCH₂—C≡CH | |
| 11.57 | H | —OCH₂—COOCH₃ | |
| 11.58 | H | —OCH(CH₃)COOCH₃ | |
| 11.59 | H | —OCH(CH₃)CH₂—S—CH₃ | |
| 11.60 | H | —OCH(CH₃)CH₂—S—C₂H₅ | |
| 11.61 | H | —OCH(CH₃)CH₂—S—C₃H₇(i) | |
| 11.62 | H | —S—CH₂—COOCH₃ | |
| 11.63 | H | —S—CH₂—COOC₂H₅ | |
| 11.64 | H | —S—CH(CH₃)COOCH₃ | |
| 11.65 | H | —S—CH(CH₃)COOC₂H₅ | |
| 11.66 | H | —S—CH(CH₃)—COO—C₃H₇(i) | |

F. FORMULATION EXAMPLES

EXAMPLE F 1.1

Formulation Examples for compounds of formula I (throughout, percentages are by weight)

| (a) Emulsifiable concentrates | (a) | (b) | (c) |
|---|---|---|---|
| a compound of Tables 1 to 11 | 25% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (b) Solutions | (a) | (b) | (c) |
|---|---|---|---|
| a compound of Tables 1 to 11 | 80% | 10% | 5% |
| ethylene glycol monomethyl ether | 20% | — | — |
| polyethylene glycol (mol.wt. 400) | — | 70% | — |
| N-methyl-2-pyrrolidone | — | 20% | 5% |
| epoxidised coconut oil | — | — | 90% |

These solutions are suitable for application in the form of microdrops.

| (c) Granulates | (a) | (b) |
|---|---|---|
| a compound of Tables 1 to 11 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (d) Dusts | (a) | (b) | (c) |
|---|---|---|---|
| a compound of Tables 1 to 11 | 2% | 5% | 8% |
| highly dispersed silicic acid | 1% | 5% | 5% |
| talcum | 97% | — | 10% |
| kaolin | — | 90% | 77% |

Ready-for-use dusts are obtained by intimately mixing the carriers with the active ingredient.

| (e) Wettable powders | (a) | (b) |
|---|---|---|
| a compound of Tables 1 to 11 | 20% | 60% |
| sodium lignosulfonate | 5% | 5% |
| sodium lauryl sulfate | 3% | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (f) Extruder granulate | |
|---|---|
| a compound of Tables 1 to 11 | 10% |

-continued

| (f) Extruder granulate | |
|---|---|
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (g) Coated granulate | |
|---|---|
| a compound of Tables 1 to 11 | 3% |
| polyethylene glycol (mol.wt. 200) | 3% |
| kaolin | 94% |

The finely ground active ingredient is uniformly applied, in a mixer, to the kaolin moistened with polyethylene glycol. Non-dusty coated granulates are obtained in this manner.

| (h) Suspension concentrate | |
|---|---|
| a compound of Tables 1 to 11 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

Example B1

Preemergence herbicidal action

Immediately after sowing seeds in flower pots of 12–15 cm diameter, the surface of the soil is treated with an aqueous spray mixture corresponding to a rate of application of 500, 250 or 125 g a.i./ha. The pots are left to stand in a greenhouse at a temperature of 22°–25° C. and 50–70% relative humidity.

After 3 weeks the herbicidal activity is evaluated on a scale from 1 to 9 (1=total damage, 9=no activity) in comparison with an untreated control group.

Ratings of 1 to 4 (especially 1 to 3) indicate good to very good herbicidal activity. Ratings of 6 to 9 (especially of 7 to 9) indicate good tolearnce (especially by cultivated plants).

In this test, the compounds of Tables 1 to 11 have good to very good herbicidal activity, while being well tolerated by cultivated plants.

TABLE 12

| Test plant | Rate of application [g/ha] | | |
|---|---|---|---|
| | 500 | 250 | 125 |
| barley | 8 | 9 | 9 |
| maize | 8 | 9 | 9 |
| rice (seed rice) | 9 | 9 | 9 |
| soybeans | 9 | 9 | 9 |
| cotton | 9 | 9 | 9 |
| sunflowers | 9 | 9 | 9 |
| Amaranthus ret. | 1 | 1 | 1 |
| Abutilon | 1 | 1 | 1 |
| Solanum nigrum | 1 | 1 | 1 |
| Viola tricolor | 1 | 1 | 1 |
| Veronica Sp. | 1 | 1 | 1 |

EXAMPLE B2

Postemergence herbicidal action (contact herbicide)

A number of weeds, both mono- and dicots, are sprayed postemergence in the 4- to 6-leaf stage with an aqueous dispersion of the test compound at a rate of 500, 250, 125 and 60 g per hectare and kept at 24°–26° C. and 45–60% relative humidity. The test is evaluated 15 days later in accordance with the rating indicated above.

In this test too, the compounds of Table 1 to 11 have good to very good herbicidal activity.

EXAMPLE B3

Herbicidal action in water rice (paddy rice)

The weeds Echinocloa crus galli and Monocharia vag., which occur in water, are sown in plastic beakers (surface: 60 cm$^2$; volume: 500 ml). After sowing, the beakers are filled with water up to the surface of the soil. Three days after sowing, the water level is increased to slightly above the soil surface (3–5 mm). Application is made 3 days after sowing by spraying the beakers with an aqueous emulsion of the test compounds at a rate of application of 0.5 to 4 kg of active ingredient per hectare. The beakers are then kept in the greenhouse under optimum growth conditions for rice weeds, i.e. at 25°–30° C. and at high humidity. The evaluation of the tests takes place 3 weeks after application.

The compounds of Preparatory Example 1 damage the weeds in this test, but not the rice.

What is claimed is:

1. A compound of formula I $$\text{(I)}$$

wherein
R$^1$ and R$^2$, taken together, are a (CH$_2$)$_4$ chain which may be substituted by one or two (C$_1$–C$_4$)-alkyl groups;
X is halogen;
A is O—R$^4$;
R$^4$ is (C$_1$–C$_8$)-alkyl.

2. A compound according to claim 1, wherein
R$^1$ and R$^2$, taken together, are a (CH$_2$)$_4$ chain which may be substituted by a (C$_1$–C$_4$)-alkyl group;
X is fluorine; chlorine; or bromine;
a is O—R$^4$;
R$^4$ is (C$_1$–C$_5$)-alkyl.

3. A compound according to claim 1, wherein $R^1$ and $R^2$, taken together, are a $(CH_2)_4$ chain which may be substituted by a methyl group;

X is fluorine; or chlorine;

A is $-O-R_4$;

$R^4$ is $(C_1-C_5)$-alkyl.

4. A compound according to claim 1, wherein X is fluorine.

5. A compound according to claim 1, wherein $R^4$ is isopropyl.

6. A compound according to claim 1, which is 2-(4-cyano-2-fluoro-5-isopropoxyphenyl)-5-methyl-4,5,6,7-tetrahydroisoindole-(2H)1,3-dione, or 2-(4-cyano-2-fluoro-5-isopropoxyphenyl)-4,5,6,7-tetrahydroisoindole-(2H)1,3-dione.

7. A herbicidal or plant growth regulating composition which comprises as active ingredient a herbicidally or growth regulatingly effective amount of a compound as claimed in claim 1, together with an inert adjuvant or carrier.

* * * * *